US009757084B2

(12) United States Patent
Sgouros et al.

(10) Patent No.: US 9,757,084 B2
(45) Date of Patent: Sep. 12, 2017

(54) METHOD AND SYSTEM FOR ADMINISTERING RADIOPHARMACEUTICAL THERAPY (RPT)

(75) Inventors: George Sgouros, Ellicott City, MD (US); Robert Hobbs, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1014 days.

(21) Appl. No.: 13/335,565

(22) Filed: Dec. 22, 2011

(65) Prior Publication Data

US 2013/0165732 A1    Jun. 27, 2013

(51) Int. Cl.
| | |
|---|---|
| *G01T 1/02* | (2006.01) |
| *A61B 6/00* | (2006.01) |
| *A61N 5/10* | (2006.01) |
| *A61B 6/03* | (2006.01) |

(52) U.S. Cl.
CPC ............ *A61B 6/5217* (2013.01); *A61B 6/508* (2013.01); *A61N 5/103* (2013.01); *A61N 5/1039* (2013.01); *A61B 6/032* (2013.01); *A61B 6/037* (2013.01); *A61B 6/4258* (2013.01); *A61N 2005/1021* (2013.01); *A61N 2005/1052* (2013.01)

(58) Field of Classification Search
CPC ... A61N 5/00; A61N 5/02; A61N 5/10; A61N 5/1039; A61N 5/1064; A61N 2005/1055
USPC ........ 250/363.02, 370.07, 303; 600/1–3, 300
See application file for complete search history.

(56) References Cited

U.S. PATENT DOCUMENTS

| | | | |
|---|---|---|---|
| 5,337,231 A | 8/1994 | Nowak et al. | |
| 5,870,697 A | 2/1999 | Chandler et al. | |
| 6,090,365 A | 7/2000 | Kaminski et al. | |
| 6,251,362 B1 * | 6/2001 | Wahl et al. ................ | 424/1.11 |
| 6,560,311 B1 | 5/2003 | Shepard | |

(Continued)

FOREIGN PATENT DOCUMENTS

| | | |
|---|---|---|
| WO | WO 99/62565 | 12/1999 |
| WO | WO 2004/067091 | 8/2004 |

OTHER PUBLICATIONS

Tremoleda et al., Imaging technologies for preclinical models of bone and joint disorders, EJNMMI Research 2011, 1:11.*

(Continued)

*Primary Examiner* — David Porta
*Assistant Examiner* — Djura Malevic
(74) *Attorney, Agent, or Firm* — DLA Piper LLP US

(57) ABSTRACT

A computerized system and method for determining an optimum amount of radiopharmaceutical therapy (RPT) to administer, comprising: performing processing associated with obtaining activity image information related to at least one agent for sub-units of at least one imaged organ from at least one detector; performing processing associated with running at least one calculation for the activity image information, using at least one computer application, to obtain absorbed dose rate image information; and performing processing associated with adding the absorbed dose rate image information, using, the at least one computer application, to obtain RPT total absorbed dose image information for the at least one imaged organ; wherein macroscopic distribution measurements that are related to microscopic or sub-unit distribution of the at least one agent are utilized.

10 Claims, 10 Drawing Sheets
(6 of 10 Drawing Sheet(s) Filed in Color)

(56) References Cited

U.S. PATENT DOCUMENTS

| | | | |
|---|---|---|---|
| 6,694,298 B1 | 2/2004 | Teagarden et al. | |
| 7,046,762 B2 | 5/2006 | Lee | |
| 7,668,662 B2 | 2/2010 | Kroll et al. | |
| 7,787,669 B2 | 8/2010 | Botterweck | |
| 8,663,083 B2* | 3/2014 | Georgi et al. | 600/1 |
| 2002/0046010 A1 | 4/2002 | Wessol et al. | |
| 2003/0219098 A1 | 11/2003 | McNutt et al. | |
| 2004/0131587 A1* | 7/2004 | Thomas et al. | 424/85.2 |
| 2004/0165696 A1 | 8/2004 | Lee | |
| 2004/0213737 A1* | 10/2004 | Huang et al. | 424/1.11 |
| 2005/0288869 A1 | 12/2005 | Kroll et al. | |
| 2006/0025824 A1 | 2/2006 | Freeman et al. | |
| 2006/0050839 A1 | 3/2006 | Balan et al. | |
| 2006/0058966 A1 | 3/2006 | Bruckner | |
| 2008/0247510 A1* | 10/2008 | Gertner et al. | 378/65 |
| 2009/0154644 A1 | 6/2009 | Nord et al. | |
| 2009/0234626 A1 | 9/2009 | Yu et al. | |
| 2009/0316858 A1 | 12/2009 | Nord | |
| 2010/0061607 A1* | 3/2010 | Sgouros et al. | 382/128 |
| 2010/0081857 A1* | 4/2010 | Georgi et al. | 600/1 |
| 2010/0232572 A1 | 9/2010 | Nord et al. | |
| 2011/0060602 A1 | 3/2011 | Grudzinski et al. | |
| 2011/0091014 A1 | 4/2011 | Siljamaki | |
| 2011/0153547 A1 | 6/2011 | McNutt et al. | |
| 2014/0149335 A1 | 5/2014 | McNutt et al. | |

OTHER PUBLICATIONS

Hindorf et al., EANM Dosimetry Committee guidelines for bone marrow and whole-body dosimetry, Eur J Nucl Med Mol Imaging, Published online: Apr. 22, 2010.*
David M. Loeb et al., "Dose-finding study of 153Sm-EDTMP in Patients with Poor-Prognosis Osteosarcoma", Cancer, vol. 115, No. 11, pp. 2514-2522, Jun. 1, 2009.
David M. Loeb et al. "Tandem Dosing of Samarium-153 Ethylenediamin Tetramethylene Phosphoric Acid with Stem Cell Support for Patients with High Risk Osteosarcoma", Cancer, pp. 5470-5478, Dec. 1, 2010.
Pete Anderson et al., "Samarium Lexidronam (153Sm-EDTMP): Skeletal Radiation for Osteoblastic Bone Metastases and Osteosarcoma", Expert Rev Anticancer Ther., vol. 7, No. 11, pp. 1517-1527, Nov. 2007.
I. Resche et al., "A Dose-Controlled Study of 153Sm-Ethylenediaminetetramethylenephosphonate (EDTMP) in the Treatment of Patients with Painful Bone Metastases", European Journal of Cancer, Vo. 33, No. 10, pp. 1583-1591, Sep. 1997.
Oliver Sartor et al., "Safety and Efficacy of Repeat Administration of Samarium Sm-153 Lexidronam to Patients with Metastatic Bone Pain"; Cancer, vol. 109, No. 3, pp. 637-643, Feb. 1, 2007.
Oliver Sartor et al., Samarium-153-Lexidronarn Complex for Treatment of Painful Bone Metastases in Hormone-Refractory Prostate Cancer , Urology, vol. 63, No. 5, pp. 940-945, May 2004.
Aldo N. Serafmi et al., Palliation of Pain Associated with Metastic Bone cancer Using Samarium-153 Lexidronam: A Double-Blind Placebo-Controlled Clinical Trial, Journal of Clinical Oncology, vol. 16, No. 4, pp. 1574-1581, Apr. 1998.
Peter M. Anderson et al., "Gemcitabine Radiosensitization After High-Dose Samarium for Osteoblastic Osteosarcoma", Clin Cancer Res., vol. 11, No. 19, pp. 6895-6900, Oct. 1, 2005.
Peter M. Anderson et al., High-Dose Samarium-153 Ethylene Diamine Tetramethylene Phosphonate: Low Toxicity of Skeletal Irradiation in Patients with Osteosarcoma and Bone Metastases, Journal of Clinical Oncology, vol. 20, No. 1, pp. 189-196, Jan. 1, 2002.
H. Malcolm Hudson et al., "Accelerated Image-Reconstruction Using Ordered Subsets of Projection Data", IEEE T. Med. Imaging, vol. 13, No. 4, pp. 601-609, Dec. 1994.
Robert F. Hobbs et al., "A Gamma Camera Count Rate Saturation Correction Method for Whole-Body Planar Imaging", Physics in Medicine and Biology, vol. 55, pp. 817-831. (2010).
T.S. Kehwar, "Analytical Approach to Estimate Normal Tissue Complication Probability Using Best Fit of Normal Tissue Tolerance Doses into the NTCP Equation of the Linear Quadratic Model", J. Cancer Res. Ther., vol. 1, No. 3, pp. 168-179, Sep. 2005.
Rachel K. Bodey et al., "Spatial Aspects of Combined Modality Radiotherapy", Radiotherapy and Oncology, Vo. 77, No. 3, pp. 301-309, Dec. 2005.
Yong Du et al., "Partial Volume Effect Compensation for Quantitative Brain SPECT Imaging", IEEE Transactions on Medical Imaging, vol. 24, No. 8, pp. 969-976, Aug. 2005.
Edgardo Browne et al., "Table of Radioactive Isotopes", John Wiley & Sons, pp. 90-1-90-4 and 111-1-111-4, Copyright 1986.
Jorg. Bohsung, et al, "IMRT Treatment Planning—A Comparative Inter-System and Inter-Centre Planning Exercise of the QUASIMODO Group," Radiotherapy and Oncology, vol. 76, pp. 354-361 (2005).
Anders B. Jensen, et al, "Influence of Late Side-Effects Upon Daily Life After Radiotherapy for Laryngeal and Pharyngeal Cancer," Acta Oncologica, vol. 33, pp. 487-491 (1994).
Q. Wu et al., "Algorithms and Functionality of an Intensity Modulated Radiotherapy Optimization System," Med. Phys., vol. 27, pp. 701-777 (2000).
A. Brahme, "Optimization of Stationary and Moving Beam Radiation Therapy Techniques," Radiother Oncol., vol. 12, pp. 129-140 (1988).
R. Lu at al., "Reduced-Order Parameter Optimization for Simplifying Prostate IMRT Planning," Phys. Med. Biol., vol. 52, pp. 849-870 (2007).
H. T. Chung et al., "Can All Centers Plan Intensity-Modulated Radiotherapy (IMRT) Effectively? An External Audit of Dosimetric Comparisons Between Three-Dimensional Conformal Radiotherapy and IMRT for Adjuvant Chemoradiation for Gastric Cancer," Int. J. Radiat. Oncol. Biol. Phys., vol. 71, pp. 1167-1174 (2008).
M.J. Williams et al., "Multicentre Quality Assurance of Intensity-Modulated Radiation Therapy Plans: A Precursor to Clinical Trials," Australas Radiol., vol. 51, pp. 472-479 (2007).
A.S. Reese et al., "Integral Dose Conservation in Radiotherapy," Med. Phys., vol. 36, pp. 731-740 (2009).
E. Astreinidou et al., "Level II Lymph Nodes and Radiation-Induced Xerostomia," Int. J. Radiat. Oncol. Biol. Phys., vol. 58, pp. 124-131 (2004).
B.V. Asselen et al., "The Dose to the Parotid Glands with IMRT for Oropharyngeal Tumors: The Effect of Reduction of Positioning Margins," Radiother Oncol., vol. 64, pp. 197-204 (2002).
K.A. Vineberg et al., "Is Uniform Target Dose Possible in the IMRT Plans in the Head and Neck," Int. J. Radiat. Oncol. Biol. Phys., vol. 52, pp. 1159-1172 (2002).
M.A. Hunt et al., "Geometric Factors Influencing Dosimetric Sparing of the Parotid Glands Using IMRT," Int. J. Radiat. Oncol. Biol. Phys., vol. 66, pp. 296-304 (2006).
T. Saito et al., "New Algorithms for Euclidean Distance Transformation of an n-Dimensional Digitized Picture with Applications," Pattern Recognition, vol. 27, pp. 1551-1565 (1994).
E.B. Bulter et al., "Smart (Simultaneous Modulated Accelerated Radiation Therapy) Boost: A New Accelerated Fractionation Schedule for the Treatment of Head and Neck Cancer with Intensity Modulated Radiotherapy," Int. J. Radiat. Oncol. Biol. Phys., vol. 45, pp. 21-32 (1999).
A. Eisbruch et al., Phase Study of Conformal and Intensity Modulated Irradiation for Propharyngeal Cancer. (Radiation therapy oncology group 0022, 2004).
L.B. Harrison et al., "Detailed Quality of Life Assessment in Patients Treated with Primary Radiotherapy for Cancer at the Base of the Tongue," Head & Neck, vol. 19, pp. 169-175 (1997).
K. Bjordal et al., "Quality of Life in Patients Treated for Head and Neck Cancer: A Follow-Up Study 7 to 11 Years After Radiotherapy," Int. J. Radiat. Oncol. Biol. Phys., vol. 28. pp. 847-856 (1994).
Mihael Ankerst et al., "3d Shape Histograms for Similarity Search and Classification in Saptial Databases", Proc. 6th International Symposium on Spatial Databases (SSD'99), Hong Kong, China, Lecture Notes in Computer Science, pp. 207-226, Jul. 1999.

(56) References Cited

OTHER PUBLICATIONS

Paul J. Besl, "Triangles as a Primary Representation", Object Representation in Computer Vision, Lecture Notes in Computer Science, vol. 994, pp. 191-206 (1995).
Cha Zhang, "Project—3D Model Retrieval", http://amp.ece.cmu.edu/projects/3DModelRetrieval/, Nov. 2, 2002 (6 pages).
Ding-Yun Chen et al., "On Visual Similarity Based 3D Model Retrieval", Computer Graphics Forum (EUROGRAPHICS 2003), vol. 22, No. 3, pp. 223-232 (2003).
R.E. Drzymala, "Dose-Volume Histograms", International Journal of Radiation Oncology, Biology, Physics, vol. 21, No. 1, pp. 71-78 (1991).
Andrea Frome et al., "Recognizing Objects in Range Data Using Regional Point Descriptors", Computer Vision (ECCV 2004), Lecture Notes in Computer Science, vol. 3023, pp. 224-237 (2004).
Thomas Funkhouser et al., "A Search Engine for 3D Models", ACM Transactions on Graphics (TOG), vol. 22, Issue 1, pp. 83-105, Jan. 2003.
Timothy Gatzke et al., "Curvature Maps for Local Shape Comparison", In Shape Modeling International, pp. 244-253 (2005).
James Gain et al., "Fast Polygon Mesh Querying by Example", AMC Conference SIGGRAPH'99 Conference Abstracts and Applications, pp. 241, Aug. 1999.
Berthold K.P. Horn, "Extended Gaussian Images", Proceedings of the IEEE, vol. 72, No. 12, pp. 1671-1686, Dec. 1984.
Andrew Edie Johnson et al., "Efficient Multiple Model Recognition in Cluttered 3-D Scenes", Proc. IEEE Conference on Computer Vision and Pattern, pp. 671-677 (1998).
A.E. Johnson et al.; "Using Spin-Images for Efficient Multiple Model Recognition in Cluttered 3D Scenes", IEEE Transactions on Pattern Analysis and Machine Intelligence, vol. 21, Issue 5, pp. 433-449, May 1999.
Michael Kazhdan et al., "A Reflective Symmetry Descriptor", ECCV 2002, LNCS 2351, pp. 642-656 (2002).
Robert Osada et al., "Matching 3D Models with Shape Distributions", International Conference on Shape Modeling and Applications (SMI 2001), pp. 154-166, May 2001.
Robert Osada et al., "Shape Distributions", ACM Transactions on Graphics, vol. 21, No. 4, p. 807-832, Oct. 2002.
"3D Model Search Engine", http://shape.cs.princeton.edu/search.html, Nov. 2001 (1 page).
Yossi Rubner et al., "The Earth Mover's Distance as a Metric for Image Retrieval", International Journal of Computer Vision, vol. 40, No. 2, pp. 99-121 (2000).
Dietmar Saupe et al., "3D Model Retrieval with Spherical Harmonics and Moments", DAGM 2001, LNCS 2191, pp. 392-397 (2001).
Sen Wang et al., "Conformal Geometry and its Applications on 3D Shape Matching, Recognition, and Stitching", IEE Transactions on Pattern Analysis and Machine Intelligence, vol. 29, No. 7, pp. 1209-1220, Jul. 2007.
Jaun Zhang et al., "Retrieving Articulated 3-D Models Using Medial Surfaces and Their Graph Spectra", EMMCVPR 2005, LNCS 3757, pp. 285-300 (2005).
Avraham Eisbruch et al., "Multi-Institutional Trial of Aaccellerated Hypofractionated Intensity-Modulated Radiation Therapy for Early-Stage Oropharyngeal Cancer (RTOG 00-22)", International Journal of Radiation Oncology, Biology, Physics, vol. 76, No. 5, pp. 1333-1338, Apr. 2010.
Binbin Wu et al., "Patient Geometry-Driven Information retrieval for IMRT Treatment Plan Quality Control", Med. Phys., vol. 36, No. 12, pp. 5497-5505, Dec. 2009.
Mark S. Kaminiski et al., "Pivotal Study to Iodine I 131 Tositumomab for Chemotherapy-Refractory Low-Grade or Transformed Low-Grade B-Cell Non-Hodgkin's Lymphomas", Journal of Clinical Oncology., vol. 19, No. 19, pp. 3918-3928, Oct. 1, 2001.
Julie M. Vose et al., "Multicenter Phase II Study of Iodine-131 Tositumomab for Chemotherapy-Relapsed/Refractory Low-Grade and Transformed Low-Grade B-Cell Non-Hodgkin's Lymphomas", Journal of Clinical Oncology, vol. 18, No. 6, pp. 1316-1323, Mar. 2000.
Kenneth F. Koral et al., "Volume Reduction Versus Radiation Dose for Tumors in Previously Untreated Lymphoma Patients Who Received Iodine-131 Tositumomab Therapy: Conjugate Views Compared With a Hybrid Method", Cancer, vol. 94, No. 4 (Suppl), pp. 1258-1263, Feb. 15, 2002.
Susan J. Knox et al., "Yttrium-90-Labeled Anti-CD20 Monoclonal Therapy of Recurrent B-Cell Lymphoma", Clinical Cancer Research, vol. 2, pp. 457-470, Mar. 1996.
Mark S. Kaminski et al., "Radioimmunotherapy of B-cell lymphoma with [131I]anti-B1 (anti-CD20) antibody", The New England Journal of Medicine, vol. 329, No. 7, pp. 459-465, Aug. 12, 1993.
Mark S. Kaminski et al., "Radioimmunotherapy with iodine 131I tositumomab for relapsed or refractory B-cell non-Hodgkin lymphoma: updated results and long-term follow-up of the University of Michigan experience", Blood, vol. 96, No. 4, pp. 1259-1266, Aug. 15, 2000.
Mark S. Kaminski et al., "131I-tositumomab therapy as initial treatment for follicular lymphoma", The New England Journal of Medicine, vol. 352, No. 5, pp. 441-449, Feb. 3, 2005.
Thomas E. Witzig et al., "Treatment with Ibritumomab Tiuxetan Radioimmunotherapy in Patients with Rituximab-Refractory Follicular Non-Hodgkin's Lymphoma", Journal of Clinical Oncology, vol. 20, No. 15, pp. 3262-3269, Aug. 1, 2002.
Raymond R. Raylman et al., "Magnetically enhanced radionuclide therapy", Journal of Nuclear Medicine, vol. 35, No. 1, pp. 157-163, Jan. 1994.
Donald J. Buchsbaum et al., "Improved delivery of radiolabeled anti-B1 monoclonal antibody to Raji lymphoma xenografts by predosing with unlabeled anti-B1 monoclonal antibody", Cancer Research, vol. 52, pp. 637-642, Feb. 1, 1992.
Kenneth F. Koral, "CT-SPECT fusion plus conjugate views for determining dosimetry in iodine-131-monoclonal antibody therapy of lymphoma patients", The Journal of Nuclear Medicine, vol. 35, No. 10, pp. 1714-1720, Oct. 1994.
T.E. Wheldon et al., "The curability of tumours of differing size by targeted radiotherapy using 131I or 90Y", Radiotherapy and Oncology, vol. 21, pp. 91-99. (1991).
Raymond R. Raylman et al., "Magnetically-enhanced radionuclide therapy (MERiT): in vitro evaluation", Int. J. Radiation Oncology Biol. Phys., vol. 37, No. 5, pp. 1201-1206 (1997).
Raymond R. Raylman et al., "Magnetically enhanced protection of bone marrow from beta particles emitted by bone-seeking radionuclides: theory of application", Medical Physics, vol. 22, No. 8, pp. 1285-1292, Aug. 1995.
Raya S. Brown et al., "Intra-tumoral microdistribution of 131I-labelled in patients with B-cell lymphoma following radioimmunotherapy", Nuclear Medicine & Biology, vol. 24, pp. 657-663 (1997).
S. Piantadosi et al., "Practical implementation of a modified continual reassessment method for dose-finding trials", Cancer Chemother Phamacol, vol. 41, pp. 429-436 (1998).
G.A. Wiseman et al., "Radiation dosimetry results from a Phase II trial of ibritumomab tiuxetan (Zevalin) radioimmunotherapy for patients with non-Hodgkin's lymphoma and mild thrombocytopenia", Cancer Biotherapy & Radiopharmaceuticals, vol. 18, No. 2, pp. 165-178, Apr. 2003.
Richard L. Wahl et al., "Patient-Specific Whole-Body Dosimetry: Principles and a Simplified Method for Clinical Implementation", The Journal of Nuclear Medicine, vol. 39, No. 8 (Suppl), pp. 14S-20S, Aug. 1998.
Elienne Garin et al., "Effect of a 188 Re-SSS lipiodol/131I-lipidol mixture, 188 Re-SSS lipiodol alone or 131I-lipiodol alone on the survival of rats with hepatocellular carcinoma", Nuclear Medicine Communications, vol. 27, No. 4, pp, 363-369, Apr. 2006.
A. Lechner et al., "Targeted Radionuclide therapy: theoretical study of the relationship between tumour control probability and tumour radius for a 32 P/33 P radionuclide cocktail", Physics in Medicine and Biology, vol. 53, No. 7, pp. 1961-1974, Mar. 18, 2008.
Linda Villard et al., "Cohort Study of Somatostatin-Based Radiopeptide Therapy With [90Y-DOTA]-TOC Versus [90Y-

(56) References Cited

OTHER PUBLICATIONS

DOTA]-TOC Plus [177Lu-DOTA]-TOC in Neuroendocrine Cancers", Journal of Clinical Oncology, vol. 30, No. 10, pp. 1100-1106, Apr. 1, 2012.
Greg L. Plosker et al., "Rituximab: A Review of its Use in Non-Hodgkin's Lymphoma and Chronic Lymphocytic Leukaemia", Drugs, vol. 63, No. 8, pp. 803-843 (2003).
Gillian M. Keating, "Spotlight on Rituximab in Chronic Lymphocytic Leukemia, Low-Grade or Follicular Lymphoma, and Diffuse Large B-Cell Lymphoma", BioDrugs, vol. 25, No. 1, pp. 55-61, Feb. 2011.
Thomas E. Witzig, "Treatment recommendations for Radioimmunotherapy in Follicular Lymphoma: A Consensus Conference Report", Leuk. Lymphoma, vol. 52, No. 7, pp. 1188-1199, Jul. 2011.
Peter Johnson et al., "The Mechanisms of Action of Rituximab in the Elimination of Tumor Cells", Seminars in Oncology, vol. 30, No. 1, Suppl 2, pp. 3-8, Feb. 2003.
Oliver W. Press et al., "Treatment of Refractory Non-Hodgkin's Lymphoma with Radiolabeled MB-1 (anti-CD37) Antibody", Journal of Clinical Oncology, vol. 7, No. 8, pp. 1027-1038, Aug. 1989.
Oliver W. Press et al., "Phase II Trial of 131I-B1 (anti-CD20) Antibody Therapy with Autologous Stem Cell Transplantation for Relapsed B Cell Lymphomas", The Lancet, vol. 346, No. 8971, pp. 336-340, Aug. 5, 1995.
E. Frey et al., "Estimation of Post-Therapy Marrow Dose Rate in Myeloablative Y-90 Ibritumomab Tiuxetan Therapy", J. Nucl. Med., vol. 47, No. Suppl 1, pp. 156P (2006).
Richard Wahl et al., "Organ Dosimetry Dose Escalation of Yttrium 90 Ibritumomab Tiuxetan radioimmunotherapy (90Y IT) Stem Cell Transplantation (ASCT) in Patients with Non-Hodgkin's Lymphoma (NHL)", The Journal of Nuclear Medicine, vol. 47, Supplement 1, pp. 97P (2006) (2 pages).
Ian M. Besse et al., "Modeling Combined Radiopharmaceutical Therapy: A Linear Optimization Framework", Technology in Cancer Research and Treatment, vol. 8, No. 1, pp. 51-60, Feb. 2009.
Hanan Amro et al., "Methodology to Incorporate Biologically Effective Dose and Equivalent Uniform Dose in Patient-Specific 3-Dimensional Dosimetry for Non-Hodgkin Lymphoma Patients Targeted with 131I-Tositumomab Therapy", The Journal of Nuclear Medicine, vol. 51, No. 4, pp. 654-659, Apr. 2010.
Robert F. Hobbs et al., "A Treatment Planning Method for Sequentially Combining Radiopharmaceutical Therapy and External radiation Therapy", Int. J. Radiation Oncology Biol. Phys., vol. 80, No. 4, pp. 1256-1262, (2011).
Sebastien Baechler et al., "Extension of the Biological Effective Dose to the MIRD Schema and Possible Implications in Radionuclide Therapy Dosimetry", Med. Phys., vol. 35, No. 3, pp. 1123-1134, Mar. 2008.
Amr Aref et al., "Radiobiological Characterization of Two Human Chemotherapy-Resistant intermediate Grade Non-Hodgkin's Lymphoma Cell Lines", Radiation Oncology Investigations, vol. 7, pp. 158-162 (1999).
J. Van Dyk et al., "Radiation-induced Lung Damage: Dose-Time-Fractionation Considerations", Radiotherapy and Oncology, vol. 14, pp. 55-69 (1989).
Bin He et al., "Comparison of Organ Residence time estimation Methods for Radioimmunotherapy Dosimetry and Treatment Planning—Patient Studies", Med. Phys., vol. 36, No. 5, pp. 1595-1601, May 2009.
Sunil Krishnan et al., "Conformal Radiotherapy of the Dominant Liver Metastasis: A Viable Strategy for Treatment of Unresectable Chemotherapy Refractory Colorectal Cancer Liver Metastases", American Journal of Clinical Oncology, vol. 29, No. 6, pp. 562-567, Dec. 2006.
Sebastien Baechler et al., "Three-Dimensional Radiobiological Dosimetry of Kidneys for Treatment Planning in Peptide Receptor Radionuclide Therapy" Med. Phys., vol. 29, No. 10, pp. 6118-6128, Oct. 2012.
Massimiliano Pacilio et al., "A Theoretical Dose-Escalation Study Based on Biological Effective Dose in Radioimmunotherapy with (90)Y-ibritumomab Tiuxetan (Zevalin)", Eur. J. Nucl. Med. Mol. Imaging, vol. 37, pp. 862-873, (2010).
J. Kotzerke et al., "Radioimmunoconjugates in Acute Leukemia Treatment: The Future is Radiant", Bone Marrow Transplantation, vol. 36, pp. 1021-1026, Oct. 10, 2005.
J.A. O'Donoghue et al., "Relationships Between Tumor Size and Curability for Uniformly Targeted Therapy with Beta-Emitting Radionuclides", The Journal of Nuclear Medicine, vol. 36, No. 10, pp. 1902-1909, Oct. 1995.
Jolanta Kunikowska et al., "Clinical Results of Radionuclide Therapy of Neuroendocrine Tumours with 90Y-DOTATATE and Tandem 90Y/177 Lu-DOTATATE: Which is Better Therapy Option?", Eur. J. Nucl. Med. Mol. Imaging, vol. 38, pp. 1788-1797, May 7, 2011.
Mark T. Madsen et al., "Potential Increased Tumor-Dose Delivery with Combined 131I-MIBG and 90Y-DOTATOC Treatment in Neuroendocrine Tumors: A Theoretic Model", The Journal of Nuclear Medicine, vol. 47, No. 4, pp. 660-667, Apr. 2006.
Thomas A. Davis et al., "The Radioisotope Contributess Significantly to the Activity of Radioimmunotherapy", Clinical Cancer Research, vol. 10, pp. 7792-7798, Dec. 7, 2004.
Thomas E. Witzig et al., "Randomized Controlled Trial of Yttrium-90—Labeled Ibritumomab Tiuxetan Radioimmunotherapy Versus Rituximab Immunotherapy for Patients With Relapsed or Refectory Low-Grade, Follicular, or Transformed B-Cell non-Hodgkin's Lymphoma", Journal of Clinical Oncology, vol. 20, No. 10, pp. 2453-2463, May 15, 2002.
Oliver W. Press et al., "Radiolabeled-Antiboy Therapy of B-Cell Lymphoma with Autologous Bone Marrow Support", The New England Journal of Medicine, vol. 329, No. 17, pp. 1219-1224, Oct. 21, 1993.
Ajay K. Gopal et al., "High Dose [131I] Tositumomab (anti-CD20) Radioimmunotherapy and Autologous Hematopoietic Stem-Cell Transplantation for Adults ≥ 60 Years Old with Relapsed or Refactory B-Cell Lymphoma", Journal of Clinical Oncology, vol. 25, No. 11, pp. 1396-1402, Apr. 10, 2007.
Ajay K. Gopal et al., "High-Dose Radioimmunotherapy Versus Conventional High-Dose Therapy and Autologous Hematopoietic Stem Cell Transplantation for Relapsed Follicular Non-Hodgkin Lymphoma: A Multivariable Cohort Analysis", Blood, vol. 102, pp. 2351-2357, Oct. 1, 2003.
Amrita Krishnan et al., "Phase II Trial of a Transplantation Regimen of Yttrium-90 Ibritumomab Tiuxetan and High-Dose Chemotherapy in Patients with Non-Hodgkin's Lymphoma", Journal of Clinical Oncology, vol. 26, No. 1, pp. 90-95, Jan. 1, 2008.
Jane N. Winter et al., "Yttrium-90 Ibritumomab Tiuxetan Doses Calculated to Deliver up to 15 Gy to Critical Organs May Be Safely Combined With High-Dose BEAM and Autologous Transplantation in Relapsed or Refractory B-Cell Non-Hodgkin's Lymphoma", Journal of Clinical Oncology, vol. 27, No. 10, pp. 1653-1659, Apr. 1, 2009.
Hong Song et al., "Therapuetic Potential of 90Y- and 131I-Labeled Anti-CD20 Monoclonal Antibody in Treating Non-Hodgkin's Lymphoma with Pulmonary Involvement: A Monte Carlo-Based Dosimetric Analysis", The Journal of Nuclear Medicine, vol. 48, No. 1, pp. 150-157, Jan. 2007.
Gregory A. Wiseman et al., "Phase I/II 90Y-Zevalin (Yttrium-90 Ibritumomab Tiuxetan, IDEC-Y2B8) Radioimmunotherapy Dosimetry Results in Relapsed or Refractory Non-Hodgkin's Lymphoma", European Journal of Nuclear Medicine, vol. 27, No. 7, pp. 766-777, Jul. 2000.
Raffaella Barone et al., "Patient-Specific Dosimetry in Predicting Renal Toxicity with 90Y-DOTATOC: Relevance of Kidney Volume and Dose Rate in Finding a Dose-Effect Relationship", The Journal of Nuclear Medicine, vol. 46, No. 1 (Suppl), pp. 99S-106S, Jan. 2005.
Barry W. Wessels et al., "MIRD Pamphlet No. 20: The Effect of Model Assumptions on Kidney Dosimetry and Response—Implications for Radionuclide Therapy", The Journal of Nuclear Medicine, vol. 49, No. 11, pp. 1884-1899, Nov. 2008.

(56) References Cited

OTHER PUBLICATIONS

Lidia Strigari et al., "Efficacy and Toxicity Related to Treatment of Hepatocellular Carcinoma with 90Y-SIR Spheres: Radiobiologic Considerations", The Journal of Nuclear Medicine, vol. 51, No. 9, pp. 1377-1385, Sep. 2010.

Yuni K. Dewarala et al., "131I-Tositumomab Radioimmunotherapy: Initial Tumor Dose—Response Results Using 3-Dimensional Dosimetry Including Raditobiologic Modeling", The Journal of Nuclear Medicine, vol. 51, No. 7, pp. 1155-1162, Jul. 2010.

Mahila E. Ferrari et al., "3D Dosimetry in Patients with Early Breast Cancer Undergoing Intraopeative Avidination for Radionuclide Therapy (IART) Combined with External Beam Radiation Therapy", Eur. J. Nucl. Med. Mol. Imaging, vol. 39, pp. 1702-1711 (2012).

Marta Cremonesi et al., "Radioembolisation with 90Y-Microspheres: Dosimetric and Radiobiological Investigation for Multi-Cycle Treatment", Eur. J. Nucl. Med. Mol. Imaging, vol. 35, pp. 2088-2096 (2008).

Roger W. Howell et al., "Application of the Linear-Quadratic Model to Radioimmunotherapy: Further Support for the Advantage of Longer-Lived Radionuclides", The Journal of Nuclear Medicine, vol. 35, No. 11, pp. 1861-1869, Nov. 1994.

Siyada N.F. Rizvi et al., "Biodistribution, Radiation Dosimetry and Scouting of 90Y-Ibritumomab Tiuxetan Therapy in Patients with Relapsed B-Cell Non-Hodgkin's Lymphoma Using 89Zr-Ibritumomab Tiuxetan and PET", Eur. J. Nucl. Med. Mol. Imaging, vol. 39, pp. 512-520 (2012).

George Sgouros et al., "Patient-Specific, 3-Dimensional Dosimetry in Non-Hodgkin's Lymphoma Patients Treated with 131I-Anti-B1 Antibody: Assessment of Tumor Dose—Response", The Journal of Nuclear Medicine, vol. 44, No. 2, pp. 260-268, Feb. 2003.

Heather A. Jacene et al., "Comparison of 90Y-Ibritumomab Tiuxetan and 131I-Tositumomab in Clinical Practice", The Journal of Nuclear Medicine, vol. 48, No. 11, pp. 1767-1776, Nov. 2007.

Hong Song et al., "213Bi (α-Emitter)-Antibody Targeting of Breast Cancer Metastases in the neu-N Transgenic Mouse Model", Cancer Res, vol. 68, No. 10, pp. 3873-3880, May 15, 2008.

Abstract of V.J. Lewinton et al., "Alpharadin, a Novel, Targeted Approach for Treatment of Bone Metastases from CRPC-Calculated Alpha-Particle Dosimetry Compared to a Favorable Clinical Safety Profile", ASCO Genitourinary Cancers Symposium, San Francisco, CA, USA (2 pages) (2010).

V.J. Lewinton et al., "Alpharadin, a Novel, Targeted Approach for Treatment of Bone Metastases from CRPC-Calculated Alpha-Particle Dosimetry Compared to a Favorable Clinical Safety Profile", ASCO Genitourinary Cancers Symposium, San Francisco, CA, USA (1 page) (2010).

George Sgouros et al., "Pharmacokinetics and dosimetry of an alpha-particle emitter labeled antibody: 213Bi-HuM195 (anti-CD33) in patients with leukemia", The Journal of Nuclear Medicine, vol. 40, No. 11, pp. 1935-1946, Nov. 1999.

M. Cristy et al., "ORNL/TM-838/V1: Specific Absorbed Fractions of Energy at Various Ages for Internal Photon Sources", Oak Ridge National Laboratory, Apr. 1987 (100 pages).

J. Schwartz et al., "Renal Uptake of Bismuth-213 and its Contribution to Kidney Radiation Dose Following Administration of Actinium-225-Labeled Antibody", Physics in Medicine Biology, vol. 56, pp. 721-733, Feb. 7, 2011.

Robert F. Hobbs et al. "A Model of Cellular Dosimetry for Macroscopic Tumors in Radiopharmaceutical Therapy", Med. Phys., vol. 38, No. 6, pp. 2892-2903, Jun. 2011.

Dinyar B. Bhathena, "Glomerular Size and the Association of Focal Glomerulosclerosis in Long-Surviving Human Renal Allografts", Journal of the American Society of Nephrology, vol. 4, No. 6, pp. 1316-1326, Dec. 1993.

Loevinger R, Budinger TF, Watson EE. MIRD Primer for Absorbed Dose Calculations. New York, NY, USA: The Society of Nuclear Medicine, Inc.; 1991 (141 Pages).

Thomas M. Behr et al., "Correlation of Red Marrow Radiation Dosimetry with Myelotoxicity: Empirical Factors Influencing the Radiation-Induced Myelotoxicity of Radiolabeled Antibodies, Fragments and Peptides in Pre-Clinical and Clinical Settings", Cancer Biotherapy and Radiopharmaceuticals, vol. 17, No. 4, pp. 445-464, Aug. 2002.

Jostein Dahle et al. "Relative Biologic Effects of Low-Dose-Rate Alpha-Emitting 227Th-Rituximab and Beta-Emitting 90Y-Tiuexetan-Ibritumomab Versus External Beam X-Radiation", Int. J. Radiation Oncology Biol. Phys., vol. 72, No. 1, pp. 186-192, Sep. 2008.

W.S. Snyder et al., ""S," Absorbed Dose per Unit Cumulated Activity for Selected Radionuclides and Organs", MIRD Pamphlet No. 11, New York, NY, USA: Society of Nuclear Medicine; Oct. 1975 (69 pages).

Wesley E. Bolch et al., "MIRD Pamphlet No. 17: The Dosimetry of Nonuniform Activity Distributions--Radionuclide S Values at the Voxel Level", The Journal of Nuclear Medicine, vol. 40, No. 1, pp. 11S-36S, Jan. 1999.

Michael G. Stabin et al. "OLINDA/EXM: The Second-Generation Personal Computer Software for Internal Dose Assessment in Nuclear Medicine", The Journal of Nuclear Medicine, vol. 46, No. 6, pp. 1023-1027, Jun. 2005.

George Sgouros et al., "MIRD Pamphlet No. 22 (abridged): Radiobiology and Dosimetry of Alpha-Particle Emitters for Targeted Radionuclide Therapy", The Journal of Nuclear Medicine, vol. 51, No. 2, pp. 311-328, Feb. 2010.

Michael R. McDevitt et al., "Radioimmunotherapy with Alpha-Emitting Nuclides", European Journal of Nuclear Medicine, vol. 25, No. 9, pp. 1341-1351, Sep. 1998.

Gamal Akabani et al., "Microdosimetric Analysis of Alpha-Particle-Emitting Targeted Radiotherapeutics Using Histological Images", The Journal of Nuclear Medicine, vol. 44, No. 5, pp. 792-805, May 2003.

Gamal Akabani et al., "Microdosimetry of Astatine-211 Using Histological Images: Application to Bone Marrow", Radiation Research, vol. 148, pp. 599-607 (1997).

E. Aurlien et al., "Exposure of Human Osteosarcoma and Bone Marrow Cells to Tumour-Targeted Alpha-Particles and Gamma-Irradiation: Analysis of Cell Survival and Microdosimetry", Int J Radiat Biol., vol. 76, No. 8, pp. 1129-1141 (2000).

Gjermund Henriksen et al., "Targeting of Osseous Sites with Alpha-Emitting 223Ra: Comparison with the Beta-Emitter 89Sr in Mice", The Journal of Nuclear Medicine, vol. 44, No. 2, pp. 252-259, Feb. 2003.

Seyed K. Imam, "Advancements in Cancer Therapy with Alpha-Emitters: a Review", Int. J. Radiation Oncology Biol. Phys., vol. 51, No. 1, pp. 271-278 (2001).

Ase M. Ballangrud et al., "Response of LNCaP Spheroids After Treatment with an Alpha-Particle Emitter (213Bi)-Labeled Anti-Prostate-Specific Membrane Antigen Antibody (J591)1", Cancer Research, vol. 61, pp. 2008-2014, Mar. 1, 2001.

G.W. Barendsen et al., "Irradiation of Human Cells in Tissue Culture with Alpha-Rays, Beta-Rays and X-Rays", International Journal of Radiation Biology and Related Studies in Physics Chemistry and Medicine, vol. 2, No. 4, pp. 441-443, Oct. 1960.

J. L. Humm, "A Microdosimetric Model of Astatine-211 Labeled Antibodies for Radioimmunotherapy", Int J Radiation Oncology Biol. Phys., vol. 13, No. 11, pp. 1767-1773, Nov. 1987.

Michael R. McDevitt et al., "Tumor Therapy with Targeted Atomic Nanogenerators", Science, vol. 294, pp. 1537-1540, Nov. 16, 2001.

Jaspreet Singh Jaggi et al., "Efforts to Control the Errant Products of a Targeted in Vivo Generator", Cancer Research, vol. 64, No. 11, pp. 4888-4895, Jun. 1, 2005.

George Sgouros, "Long-Lived Alpha Emitters in Radioimmunotherapy: The Mischievous Progeny", Cancer Biotherapy Radiopharmaceuticals, vol. 15, No. 3, pp. 219-221 (2000).

Michael R. Zalutsky et al., "Targeted Alpha-Particle Radiotherapy with 211 At-Labeled Monoclonal Antibodies", Nuclear Medicine and Biology, vol. 34, pp. 779-785 (2007).

Michael R. Zalutsky et al., "Radioimmunotherapy with Alpha-Particle Emitting Radioimmunoconjugates", Acta Oncologica, vol. 35, No. 3, pp. 373-379 (1996).

(56) References Cited

OTHER PUBLICATIONS

Michael R. McDevitt et al., "An Alpha-Particle Emitting Antibody ([213Bi]J591) for Radioimmunotherapy of Prostate Cancer", Cancer Research, vol. 60, pp. 6095-6100, Nov. 1, 2000.

Gjermund Henriksen et al., "Significant Antitumor Effect from Bone-Seeking, Alpha-Particle-Emitting (223)Ra Demonstrated in an Experimental Skeletal Metastases Model", Cancer Research, vol. 62, pp. 3120-3125, Jun. 1, 2002.

L. Arazi et al., "The Treatment of Solid Tumors by Alpha Emitters Released from (224)Ra-Loaded Sources-Internal Dosimetry Analysis", Physics in Medicine and Biology, vol. 55, pp. 1203-1218 (2010).

Hakan Andersson et al., "Intraperitoneal Alpha-Particle Radioimmunotherapy of Ovarian Cancer Patients: Pharmacokinetics and Dosimetry of (211)At-MX35 F(ab')2—A Phase I Study", The Journal of Nuclear Medicine, vol. 50, No. 7, pp. 1153-1160, Jul. 2009.

Abstract of M. R. Zalutsky et al., "Radioimmunotherapy of Recurrent Glioma Patients Using Alpha-Particle Emitting Astatine-211 Labeled Chimeric Anti-Tenascin Monoclonal Antibody", The 48th SNM Annual Meeting, A Supplement to The Journal of Nuclear Medicine, vol. 42, No. 5, pp. 121P-122P, May 2001, Supplement.

Michael R. Zalutsky et al., "Clinical Experience with Alpha-Particle Emitting 211At-Labeled Chimeric Antitenascin Monoclonal Antibody 8106", The Journal of Nuclear Medicin, vol. 49, No. 1, pp. 30-38, Jan. 2008.

Joseph G. Jurcic et al., Targeted Alpha Particle Immunotherapy for Myeloid Leukemia, Blood, vol. 100, No. 4, pp. 1233-1239, Aug. 15, 2002.

Abstract of J.G. Jurcic et al., "Alpha-Particle Immunotherapy for Acute Myeloid Leukemia (AML) with Bismuth-213 and Actinium-225", Cancer Biother Radiopharm., vol. 21, No. 4, pp. 396, Sep. 25, 2006.

Stefan Kneifel et al., "Local Targeting of Malignant Gliomas by the Diffusible Peptidic Vector 1,4,7,10-Tetraazacyclododecane-1-Glutaric Acid-4,7,10-Triacetic Acid-Substance P", Clin. Cancer Res., vol. 12, No. 12, pp. 3843-3850, Jun. 15, 2006.

Knut Liepe, "Alpharadin, a 223Ra-Based Alpha-Particle-Emitting Pharmaceutical for the Treatment of Bone Metastases in Patients with Cancer", Current Opinion in Investigational Drugs, vol. 10, No. 12, pp. 1346-1358 (2009).

Oyvind S. Bruland et al., "High-Linear Energy Transfer Irradiation Targeted to Skeletal Metastases by the Alpha-Emitter 223Ra: Adjuvant or Alternative to Conventional Modalities?", Clin. Cancer Res., vol. 12, No. 20 Suppl, pp. 6250s-6257s, Oct. 15, 2006.

E. Menapace et al., "Comparison Between Theoretical Calculation and Experimental Results of Excitation Functions for Production of Relevant Biomedical Radionuclides", .CP769, International Conference on Nuclear Data for Science and Technolgoy, pp. 1638-1641 (2005).

T.R. Butz et al., "233U Disposition Medical Isotope Production and Building 3019 Complex Shutdown Project", 2005 NCSD Topical Meeting: Integrating Criticality Safety into the Resurgence of Nuclear Power, American Nuclear Society, Sep. 19-22, 2005 (14 pages).

Martin W. Brechbiel, "Targeted Alpha Therapy: Past, Present, future?", Dalton Transactions, pp. 4918-4928 (2007).

L.I. Guseva et al., "Development of a Tandem Generator System 229Th/225Ac/213Bi for Repeated Production of Short-Llived Alpha-Emitting Radionuclides", Radiochemistry, vol. 51, No. 2, pp. 169-174, (2009).

Fred Ramsey et al., "Converting an AEG Cyclotron to H-Acceleration and Extraction", CP1009, Application of Acelerators in Research and Industry: 20th International Conference, pp. 500-503 (2009).

L.I. Guseva et al., "A Ggenerator System for Production of Medical Alpha-Radionuclides Ac-225 and Bi-213", Journal of Radioanalytical and Nuclear Chemistry, vol. 285, pp. 667-673 ( 2010).

Abstract of R. Hultborn et al. "Pharmacokinetics and Dosimetry of (211)AT-MX35 F(AB')2 in Therapy of Ovarian Cancer—Preliminary Results from an Ongoing Phase I Study", Cancer Biotherapy and Radiopharmaceuticals, vol. 21, No. 4, pp. 395, Sep. 25, 2006.

Abstract of S. Nilsson et al., "Clinical Experience and Radiation Safety of the First-in-Class Alpha-Pharmaceutical, Alpharadin (Radium-223) in Patients with Castration-Resistant Prostate Cancer (CRPC) and Bone Metastases", International Journal of Radiation Oncology Biology Physics, vol. 78, No. 3 Supplemental pp. S375-S376 (2010).

Sandra J. Horning et al., "Efficacy and Safety of Tositumomab and Iodine-131 Tositumomab (Bexxar) in B-Cell Lymphoma, Progressive After Rituximab", Journal of Clinical Oncology, vol. 23, No. 4, pp. 712-719, Feb. 1, 2005.

Thomas E. Witzig et al., "Safety of Yttrium-90 Ibritumomab Tiuxetan Radioimmunotherapy for Relapsed Low-Grade, Follicular, or Transformed Non-Hodgkin's Lymphoma", Journal of Clinical Oncology, vol. 21, No. 7, pp. 1263-1270, Apr. 1, 2003.

George Sgouros, "Bone Marrow Dosimetry for Radioimmunotherapy: Theoretical Considerations", The Jouranl of Nuclear Medicine, vol. 34, No. 4, pp. 689-694, Apr. 1993.

Christopher J. Watchman et al., "Absorbed Fractions for Alpha-Particles in Tissues of Cortical Bone", Phys. Med. Biol., vol. 54, pp. 6009-6027, Sep. 22, 2009.

Christopher J. Watchman et al., "Spatial Distribution of Blood Vessels and CD34+ Hematopoietic Stem and Progenitor Cells Within the Marrow Cavities of Human Cancellous Bone", The Journal of Nuclear Medicine, vol. 48, No. 4, pp. 645-654, Apr. 2007.

Christopher J. Watchman et al., "Absorbed Fractions for Alpha-Particles in Tissues of Trabecular Bone: Considerations of Marrow Cellularity Within the ICRP Reference Male", The Journal of Nuclear Medicine, vol. 46, No. 7, pp. 1171-1185, Jul. 2005.

James M. Brindle et al., "Correlations of Total Pelvic Spongiosa Volume with Both Anthropometric Parameters and Computed Tomography-Based Skeletal Size Measurements", Cancer Biotherapy and Radiopharmaceuticals, vol. 21, No. 4, pp. 352-363 (2006).

James M. Brindle et al., "CT Volumetry of the Skeletal Tissues", Med. Phys., vol. 33, No. 10, pp. 3796-3803, Oct. 2006.

James M. Brindle et al., "Linear Regression Model for Predicting Patient-Specific Total Skeletal Spongiosa Volume for Use in Molecular Radiotherapy Dosimetry", The Journal of Muclear Medicine, vol. 47, No. 11, pp. 1875-1883, Nov. 2006.

W.E. Botch et al., "Skeletal Absorbed Fractions for Electrons in the Adult Male: Considerations of a Revised 50-Micron Definition of the Bone Endosteum", Radiation Protection Dosimetry, vol. 127, No. 1-4, pp. 169-173, Jun. 7, 2007.

Vincent A. Bourke et al., "Spatial Gradients of Blood Vessels and Hematopoietic Stem and Progenitor Cells Within the Marrow Cavities of the Human Skeleton", Blood, vol. 114, No. 19, pp. 4077-4080, Nov. 5, 2009.

J.G. Hunt et al., "Calculation of Absorbed Fractions to Human Skeletal Tissues Due to Alpha Particles Using the Monte Carlo and 3-D Chord Based Transport Techniques", Radiation Protection Dosimetry, vol. 127, No. (1-4), pp. 223-226, Jun. 14, 2007.

Choonik Lee et al., "An Assessment of Bone Marrow and Bone Endosteum Dosimetry Methods for Photon Sources", Phys. Med. Biol., vol. 51, pp. 5391-5407, Oct. 6, 2006.

Jose C. Pichardo et al., "Method for Estimating Skeletal Spongiosa Volume and Active Marrow Mass in the Adult Male and Adult Female", The Journal of Nuclear Medicine, vol. 48, No. 11, pp. 1880-1888, Nov. 2007.

D.A. Rajon et al., "Image Segmentation of Trabecular Spongiosa by Visual Inspection of the Gradient Magnitude", Phys. Med. Biol., vol. 51, pp. 4447-4467, Aug. 22, 2006.

Dik J. Kwekkeboom et al., "Overview of Results of Peptide Receptor Radionuclide Therapy with 3 Radiolabeled Somatostatin Analogs", The Journal of Nuclear Medicine, vol. 46, No. 1 (Suppl), pp. 62S-66S, Jan. 2005.

Jean Claude Reubi et al., "Affinity Profiles for Human Somatostatin Receptor Subtypes SST1-SST5 of Somatostatin Radiotracers Selected for Scintigraphic and Radiotherapeutic use", European Jouranl of Nuclear Medicine, vol. 27, No. 3, pp. 273-282, Mar. 2000.

(56) References Cited

OTHER PUBLICATIONS

Lionel G. Bouchet et al., "MIRD Pamphlet No. 19: Absorbed Fractions and Radionuclide S Values for Six Age-Dependent Multiregion Models of the Kidney", The Journal of Nuclear Medicine, vol. 44, No. 7, pp. 1113-1147, Jul. 2003.
Hong Song et al., "Radioimmunotherapy of Breast Cancer Metastases with Alpha-Particle Emitter 225Ac: Comparing Efficacy with 213Bi and 90Y", Cancer Res., vol. 69, No. 23, pp. 8941-8948, Dec. 1, 2009.
Jaspreet Singh Jaggi et al., "Renal Tubulointerstitial Changes After Internal Irradiation with Alpha-Particle-Emitting Actinium Daughters", J. Am. Soc. Nephrol., vol. 16, pp. 2677-2689 (2005).
Jaspreet Singh Jaggi et al., "Mitigation of Radiation Nephropathy After Internal Alpha-Particle Irradiation of Kidneys", Int. J. Radiat. Oncol. Biol. Phys., vol. 64, No. 5, pp. 1503-1512 (2006).
Tom Back et al., "Glomerular Filtration Rate After Alpha-Radioimmunotherapy with 211At-MX35-F(ab')2: a Long-Term Study of Renal Function in Nude Mice", Cancer Biotherapy Radiopharmaceuticals, vol. 24, No. 6, pp. 649-658 (2009).
S. Agostinelli et al., GEANT4—A Simulation Toolkit, Nuclear Instruments and Methods in Physcis Research A, vol. 506, pp. 250-303 (2003).
M. Pacilio et al., "Differences Among Monte Carlo Codes in the Calculations of Voxel S Values for Radionuclide Targeted Therapy and Analysis of Their Impact on Absorbed Dose Evaluations", Med. Phys., vol. 35, No. 5, pp. 1543-1552, May 2009.
N. Chouin et al., "Evidence of Extranuclear Cell Sensitivity to Alpha-Particle Radiation Using a Microdosimetric Model. I. Presentation and Validation of a Microdosimetric Model", Radiation Research, vol. 171, pp. 657-663 (2009).
N. Chouin et al., "Evidence of Extranuclear Cell Sensitivity to Alpha-Particle Radiation Using a Microdosimetric Model. II. Application of the Microdosimetric Mmodel to Experimental Results", Radiation Research, vol. 171, pp. 664-673 (2009).
Robert Hobbs, "A Trabecular Model of Bone Marrow Toxicity for 223Ra Alpha-Emitter Radiopharmaceutical Therapy", The Journal of Nuclear Medicine, vol. 52 (Supplemental 1), pp. 130 (2011).
Amish P. Shah et al., "Adipocyte Spatial Distributions in Bone Marrow: Implications for Skeletal Dosimetry Models", The Journal of Nuclear Medicine, vol. 44, No. 5, pp. 774-783, May 2003.
Amish P. Shah et al., "A Paired-Image Radiation Transport Model for Skeletal Dosimetry", The Journal of Nuclear Medicine, vol. 46, No. 2, pp. 344-353, Feb. 2005.
Matthew Hough et al., "An Image-Based Skeletal Dosimetry Model for the ICRP Reference Adult Male-linternal Electron Sources", Phys. Med. Biol., vol. 56, pp. 2309-2346 (2011).
Perry B. Johnson et al., "Response Functions for Computing Absorbed Dose to Skeletal Tissues from Photon Irradiation—An Update", Phys. Med. Biol., vol. 56, pp. 2347-2365 (2011).
Sebastien Baechler et al., "Predicting Hematologic Toxicity in Patients Undergoing Radioimmunotherapy with 90Y-Ibritumomab Tiuxetan or 131I-Tositumomab", The Journal of Nuclear Medicine, vol. 51, No. 12, pp. 1878-1884, Dec. 2010.
Tom Back et al., "The Alpha-Camera: A Quantitative Digital Autoradiography Technique Using a Charge-Coupled Device for Ex Vivo High Resolution Bioimaging of Alpha-Particles", The Journal of Nuclear Medicine, vol. 51, No. 10, pp. 1616-1623, Oct. 2010.
Sui Shen et al., "A Preliminary Cell Kinetics Model of Thrombocytopenia After Radioimmunotherapy", The Journal of Nuclear Medicine, vol. 39, No. 7, pp. 1223-1229, Jul. 1998.
Gary L. Rosner et al., "Pharmacodynamic Analysis of Hematologic Profiles", Journal of Pharmacokinetics and Biopharmaceutics, vol. 22, No. 6, pp. 499-524 (1994).
Abstract of S. Baechler et al., "A Kinetic Model of Patient Platelets After Radioimmunotherapy", 55th SNM Annual Meeting, Abstract Book Supplement to The Journal of Nuclear Medicine, vol. 49, Supplement 1, pp. 48P, May 2008.
H. Song et al., "An Immunotolerant HER-2/neu Transgenic Mouse Model of Metastatic Breast Cancer", Clin. Cancer Res., vol. 14, N. 19, p. 6116-6124, Oct. 1, 2008.

International Search report issued in International Application PCT/US2007/085400, mailed Sep. 10, 2010.
Oliver W. Press et al., "A Phase I/II Trial of Iodine-131-tositumomab (anti-CD20),etoposide, cyclophosphamide, and Autologous Stem Cell Transplantation for Relapse B-Cell Lymphomas", Blood, vol. 96, No. 9, pp. 2934-2942, Nov. 1, 2000.
B. Emami et al,, "Tolerance of Normal Tissue to Therapeutic Irradiation", Int. J. Radiation Oncology Biol. Phys., vol. 21, pp. 109-122 (1991).
Roger Dale et al., "The Radiobiology of Conventional Radiotherapy and Its Application to Radionuclide Therapy", Cancer Biotherapy & Radiopharmaceuticals, vol. 20, No. 1, pp. 47-51 (2005).
Roger Dale, "Use of the Linear-Quadratic Radiobiological Model for Quantifying Kidney Response in Targeted Radiotherapy", Cancer Biotherapy & Radiopharmaceuticals, vol. 19, No. 3, pp. 363-370 (2004).
Joseph A. O'Donoghue, "Implications of Nonuniform Tumor Doses for Radioimmunotherapy", The Journal of Nuclear Medicine, vol. 40, No. 8, pp. 1337-1341, Aug. 1999.
Wesley Bolch et al., "MIRD Pamphet No. 21: A Generalized Schema for Radiopharmaceutical Dosimetry—Standaradization of Nomenclature", The Journal of Nuclear Medicine, vol. 50, No. 3, pp. 477-484, Mar. 2009.
Bin He et al., "A Monte Carlo and Physical Phantom Evaluation of Quantitative In-111 SPECT", Physics in Medicine Biology, vol. 50, pp. 4169-4185 (2005).
H. Malcolm Hudson et al., "Accelerated Image Reconstruction Using Ordered Subsets of Projection Data", IEEE Transactions on Medical Imaging, vol. 13, No. 4, pp. 601-609, Dec. 1994.
Dan J. Kadrmas et al., "Fast Implementations of Reconstruction-Based Scatter Compensation in Fully 3D SPECT Image Reconstruction", Phys. Med. Biol., vol. 43, No. 4, pp. 857-873, Apr. 1998.
Robert F. Hobbs et al., "Arterial Wall Dosimetry for Non-Hodgkin Lymphoma Patients Treated with Radioimmunotherapy", The Journal of Nuclear Medicine, vol. 51, No. 3, pp. 368-375, Mar. 2010.
Robert F. Hobbs et al., "$^{124}$I PET-Based 3D-RD Dosimetry for a Pediatric Thyroid Cancer Patient: Real-Time Treatment Planning and Methodologic Comparison", The Journal of Nuclear Medicine, vol. 50, No. 11, pp. 1844-1847, Nov. 2009.
Andrew R. Prideaux et al., "Three-Dimensional Radiobiologic Dosimetry: Application of Radiobiologic Modeling to Patient-Specific 3-Dimensional Imaging-Based Internal Dosimetry", The Journal of Nuclear Medicine, vol. 48, No. 6, pp. 1008-1016, Jun. 2007.
John F. Fowler, "The Linear-Quadratic Formula and Progress in Fractionated Radiotherapy", The British Journal of Radiology, vol. 62, No. 740, pp. 679-694, Aug. 1989.
William T. Millar, "Application of the Linear-Quadratic Model with Incomplete Repair to Radionuclide Directed Therapy", The British Journal of Radiology, vol. 64, No. 759, pp. 242-251, Mar. 1991.
D.J. Brenner et al., "The Linear-Quadratic Model and Most Other Common Radiobiological Models Result in Similar Predictions of Time-Dose Relationships", Radiation Research, vol. 150, pp. 83-91 (1998).
Robert F. Hobbs et al., "Calculation of the Biological Effective Dose for Piecewise Defined Dose-Rate Fits", Med. Phys., vol. 36, No. 3, pp. 904-907, Mar. 2009.
R. G. Dale, "The Application of the Linear-Quadratic Dose-Effect Equation to Fractionated and Protracted Radiotherapy", The British Journal of Radiology, vol. 58, No. 690, pp. 515-528, Jun. 1985.
R. K. Bodey et al., "Combining Dosimetry for Targeted Radionuclide and External Beam Therapies Using the Biologically Effective Dose", Cancer Biotherapy & Radiopharmaceuticals, vol. 18, No. 1, pp. 89-97 (2003).
Rachel K. Bodey et al., "Application of the Linear-Quadratic Model to Combined Modality Radiotherapy", Int. J. Radiation Oncology Biol. Phys., vol. 59, No. 1, pp. 228-241 (2004).
D. J. Brenner et al., "Conditions for the Equivalence of Continuous to Pulsed Low Dose Rate Brachytherapy", Int. J. Radiation Oncology Biol. Phys., vol. 20, pp. 181-190, Jan. 1991.
C. Chiesa et al., "A Practical Dead Time Correction Method in Planar Activity Quantification for Dosimetry During Radionuclide

(56) References Cited

OTHER PUBLICATIONS

Therapy", The Quarterly Journal of Nuclear Medicine and Molecular Imaging, vol. 53, No. 6, pp. 658-670, Dec. 2009.
G. Delpon et al., "Correction of Count Losses Due to Deadtime on a DST-Xli (SMVi-GE) Camera During Dosimetric Studies in Patients Injected with Iodine-131", Physics in Medicine and Biology, vol. 47, pp. N79-N90 (2002).
James A. Sorenson et al., "Methods of Correcting Anger Camera Deadtime Losses", Journal of Nuclear Medicine, vol. 17, No. 2, pp. 137-141 (1976).
Kenneth R. Zasadny et al., "Dead Time of an Anger Camera in Dual-Energy-Window-Acquisition Mode", Med. Phys., vol. 20, No. 4, pp. 1115-1120, Jul./Aug. 1993.
Indra J. Das et al., "Intensity-Modulated Radiation Therapy Dose Prescription, Recording, and Delivery: Patterns of Variability Among Institutions and Treatment Planning Systems", JNCI, vol. 100, Issue 5, pp. 300-307, Mar. 5, 2008.
Thomas Bortfeld et al, "Image-Guided IMRT", Springer, pp. V-XII, and 1-460, Copyright 2006.
U.S. Appl. No. 12/687,670.
U.S. Appl. No. 12/690,471.
U.S. Appl. No. 12/820,852.
Michael Kazhdan et al., "A Shape Relationship Descriptor for Radiation Therapy Planning", Medical Image Computing and Computer-Assisted Intervention (MICCAI 2009) LNCS 5762, Part II, pp. 100-108, Jan. 1, 2009.
International Search Report issued in International Application No. PCT/US2013/066872 dated Apr. 24, 2014.
Written Opinion issued in International Application No. PCT/US2013/066872 dated Apr. 24, 2014.
George Sgouros et al., "3-D Imaging Based, Radio Biological Dosimetry", Semin. Nucl. Med. vol. 38, No. 5, pp. 321-334, Sep. 2008.
Stephen K. Gerard et al., "131I Dosimetry and Thyroid Stunning", The Journal of Nuclear Medicine, vol. 44, No. 12, pp. 2039-2040, Dec. 2003.
Ernest L. Mazzaferri et al., "Clinical Review 128: Current Approaches to Primary Therapy for Papillary and Follicular Thyroid Cancer", The Journal of Clinical Endocrinology and Metabolism, vol. 88, No. 6, pp. 1447-1463 (2001).
Fabrice Le Gall et al., "Di-, Tri-, and Tetrameric Single Chain Fv Antibody Fragmetns Against Human CD19: Effect of Valency on Cell Binding", FEBS Letters, vol. 453, pp. 164-168 (1999).
Isabelle Clairand et al., "Dose3d: EGS4 Monte Carlo Code-Based Software for Internal Radionuclide Dosimetry", Journal of Nuclear Medicine, vol. 40, No. 9, pp. 1517-1523, Sep. 1999.
George Sgouros, "Dosimetry of Internal Emitters", The Journal of Nuclear Medicine, vol. 46, No. 1 (Suppl), pp. 18S-27S, Jan. 2005.
Robert Dorn et al., Dosimetry-Guided Radioactive Iodine Treatment in Patients with Metastatic Differentiated Thyroid Cancer: Largest Safe Dose Using a Risk-Adapted Approach, The Journal of Nuclear Medicine, vol. 44, No. 3, pp. 451-456, Mar. 2003.
Thomas M. Behr et al., "Experimetnal Studies on the Role of Antibody Fragments in Cancer Radio-immunotherapy: Influence of Radiation Dose and Dose Rate on Toxicity and Anti-Tumor Efficacy", Int. J. Cancer, vol. 77, pp. 787-795 (1998).
Katherine S. Kolbert et al., Implementation and Evaluation of Patient-Specific Three-Dimensional Internal Dosimetry, The Journal of Nuclear Medicine, vol. 38, No. 2. pp. 301-308 (Feb. 1997).
Heribert Hanscheid et al., "Iodine Biokinetics and Dosimetry in Radioiodiine Therapy of Thyroid Cancer: Procedures and Results of a Prospective International Controlled Study of Ablation After rhTSH or Hormone Withdrawal", The Journal of Nuclear Medicine, vol. 47, No. 4, pp. 648-654, Apr. 2006.
Andreas Otte et al., "Is Radiation Nephropathy Caused by yttrium-90?", The Lancet, vol. 359, pp. 979, Mar. 16, 2002.
Hong Song et al., "Lung Dosimetry for Radioiodine Treatment Planning in the Case of Diffuse Lung Metastases", The Journal of Nuclear Medicine, vol. 47, No. 12, pp. 1985-1994, Dec. 2006.

Sui Shen et al., "Model Prediction of Treatment Planning for Dose-Fractionated Radioimmunotherpary", Cancer, vol. 94, No. 4, pp. 1264-1269, Feb. 15, 2002.
J.L. Humm et al., "Nonuniformity of Turmo Dose in Radioimmunotherpary", The Journal of Nuclear Medicine, vol. 31, No. 1, pp. 75-83, Jan. 1990.
Lynne J. Lawrence et al., "Orientation of Antigen Binding Sites in Dimeric and Tirmeric Single Chain Fv Antibody Fragments", FEBS Letters, vol. 45, pp. 479-484 (1998).
George Sgouros et al., "Patient-Specific Dosimetry for 131I Thyroid Cancer Therapy Using 124I PET and 3-Dimensional-Internal Dosimetry (3D-ID) Software", The Journal of Nuclear Medicine, vol. 45, No. 8, pp. 1366-1372, Aug. 2004.
Aban Meyer Samuel et al., "Polmonary Metastases in Children and Adolescents with Well-Differentiated Thyroid Cancer", The Journal of Nuclear Medicine, vol. 39, No. 9, pp. 1531-1536, Sep. 1998.
Eric P. Cohen et al., "Radiation Nephropathy Caused by yttrium 90", The Lancet, vol. 358, pp. 1102-1103, Sep. 29, 2001.
Gerald L. DeNardo et al., "Rationales, Evidence, and Design Considerations for Fractionated Radioimmunotherapy", Cancer, vol. 94, No. 4, pp. 1332-1348, Feb. 15, 2002.
John L. Atwell et al., "scFv Multimers of the Anti-Neuraminidase Antibody NC10: Length of the Linker between VH and VL Domains Dictates Precisely the Transition Between Diabodies and Triabodies", Protein Engineering, vol. 12, No. 7, pp. 597604 (1999).
Joseph A. O'Donoghue et al., "Single-Dose Versus Fractionated Radioimmunotherapy: Model Comparisons for Uniform Tumor Dosimetry", The Journal of Nuclear Medicine, vol. 41, No. 3, pp. 538-547, Mar. 2000.
Richard J. Robbins et al., "The Evolving Role of 131I for the Treatment of Differentiated Thyroid Carcinoma", The Journal of Nuclear Medicine, vol. 46, No. 1 (Suppl), pp. 28S-37S, Jan. 2005.
Glenn D. Flux et al., "Three-Dimensional Dosimetry for Intralesional Radionuclide Therapy Using Mathematical Modeling and Multimodality Imaging", The Journal of Nuclear Medicine, vol. 38, No. 7, pp. 1059-1066, Jul. 1997.
Peter L. Roberson et al., "Three-Dimensional Reconstrcution of Monoclonal Antibody Uptake in Tumore and Calculation of Beta Dos-Rate Nonuniformity", Cancer, vol. 73, No. 3 (Suppl), pp. 912-918, Feb. 1, 1994.
Dandamudi V. Rao et al., "Time-Dose-Fractionation in Radioimmunotherapy: Implications for Selecting Radionuclides", The Journal of Nuclear Medicine, vol. 34, No. 10, pp. 1801-1810, Oct. 1993.
George Sgouros et al., "Treatment Planning for Internal Radionuclide Therapy: Three-Dimensional Dosimetry for Nonuniformly Distributed Radionuclides", The Journal of Nuclear Medicine, vol. 31, No. 11, pp. 1884-1891, Nov. 1990.
Joseph G. Rajendran et al., "Tumor Hypoxia Imaging with [F-18] Fluoromisonidazole Positron Emission Tomography in Head and Neck Cancer", Clin. Cancer Res., vol. 12, No. 18, pp. 5435-5441, Sep. 15, 2006.
Hui Zhu et al., "Tumor Pretargeting for Radioimmunodetection and Radioimmunotherapy", The Journal of Nuclear Medicine, vol. 39, No. 1, pp. 65-76, Jan. 1998.
E.E. Furhang et al., "Implementation of a Monte Carlo Dosimetry Method for Patient-Specific Internal Emitter Therapy", Med. Phys., vol. 24, No. 7, pp. 1163-1172, Jul. 1997.
Michael Stabin, "Nuclear Medicine Dosimetry", Phys. Med. Biol., vol. 51, pp. R187-R202 (2006).
An Liu et al., "Monte Carlo-Assisted Voxel Source Kernal Method (MAVSK) for Internal Beta Dosimetry", Nuclear Medicine & Biology, vol. 25, pp. 423-433 (1998).
A.K. Erdi et al., "Use of the Fast Hartley Transform for Efficient 3D Convolution in Calculation of Radiation Dose", IEEE, pp. 639-640 (1994).
Matthew J. Guy et al., "RMDP: A Dedicated Package for 131I Spect Quantification, Registration and Patient-Specific Dosimetry", Cancer Biotherapy & Radiopharmaceuticals, vol. 18, No. 1, pp. 61-69 (2003).
Marie-Anne Descalle et al., "Application of MINERVA Monte Carlo Simulations to Targeted Radionuclide Therapy", Cancer Biotherapy & Radiopharmaceuticals, vol. 18, No. 1, pp. 71-79 (2003).

(56) References Cited

OTHER PUBLICATIONS

S, Chiavassa et al., "Validation of a Personalized Dosimetric Evaluation Tool (Oedipe) for Targeted Radiotherapy Based on the Monte Carlo MCNPX Code", Phys. Med. Biol., vol. 51, pp. 601-616 (2006).
Moorthy S. Muthuswamy et al., "A Quantitave Study of Radionuclide Characteristics for Radioimmunotherapy from 3D Reconstrucions Using Serial Autoradiography", Int. J. Radiation Oncology Biol. Phys., vol. 35, No. 1, pp. 165-172 (1996).
Aiden A. Flynn et al., "Optimizing Radioimmunotherapy by Matching Dose Distributinon with Tumor Structure Using 3D Reconstructions of Serial Images", Cancer Biotherapy & Radiopharmaceuticals, vol. 16, No. 5, pp. 391-400 (2001).
Roger W. Howell et al., "Macroscopic Dosimetry for Radioimmunotherapy: Nonuniform Activity Districutions in Solid Tumors", Med. Phys., vol. 16, No. 1, pp. 66-74, Jan-Feb 1989.
Aiden A. Flynn et al., "The Nonuniformity of Antibody Distribution in the Kidney and its Influence on Dosimetry", Radiation Research, vol. 159, pp. 182-189 (2003).
Eric J. Hall et al., "Radiation Dose-Rate: A Factor of Importance in Radiobiology and Radiotherapy", The British Journal of Radiology, vol. 45, No. 530, pp. 81-97, Feb. 1972.
G.W. Barendsen et al., "Dose Fractionation, Dose Rate and ISO-Effect Relationships for Normal Tissue Responses", Int. J. Radiation Oncology Bio. Phy., vol. 8, No. 11, pp. 1981-1997, Nov. 1982.
Rulon Mayer et al., "Direct Measurement of Intratumor Dose-Rate Distributions in Experimental Xenografts Treated with 90Y-Labeled Radioimmunotherapy", Int. J. Radiation Oncology Biol. Phys., vol. 32, No. 1, pp. 147-157 (1995).
Gamal Akabani et al., "Dosimetry and Dose-Response Relationships in Newly Diagnosed Patients with Malignant Gliomas Treated with Iodine-131-Labeled Anti-Tenascin Monoclonal Antibody 8106 Therapy", Int. J. Radiation oncology Biol. Phys., vol. 46, No. 4, pp. 947-958 (2000).
A.A. Flynn et al., "Effectiveness of Radiolabelled Antibodies for Radio-Immunotherapy in a Colorectal Xenograft Model: A comparative Study Using the Linear-Quadratic Formulation", International Journal of Radiation Biology, vol. 77, No. 4, pp. 507-517 (2001).
Abstract of K.S. Kolert et al., "Display and Manipulation of SPECT and CT Studies for Radiolabeled Antibody Therapy", Cancer Biother Radiopharm, vol. 13, pp. 302 (1998).
Eli E. Furhang et al., "A Monte Carlo Approach to Patient-Specific Dosimetry", Med. Phys., vol. 23, No. 9, pp. 1523-1529, Sep. 1996.
J. Van Dyke et al., "Determination of Parameters for the Linear-Quadratic Model for Radiation-Induced Lung Damage", Int. J. Radiation oncology Biol. Phys., vol. 17, pp. 695 (1989).
Anthony Gaussen et al., "Radiosensitivity of Human Normal and Tumoral Thyroid Cells Using Fluoscence in situ Hybridization and Clonogenic Survival Assay", Int. J. Radiation oncology Biol. Phys., vol. 44, No. 33, pp. 683-691 (1999).
Cecile Challeton et al., "Characterization and Radiosensitivity at High or Low Dose Rate of Four Cell Lines Derived from Human Thyroid Tumors", Int. J. Radiation Oncology Biol. Phys., vol. 37, No. 1, pp. 163-169 (1997).
Eric C. Frey et al., "Application of Task-Based Measures of Image Quality to Optimization and Evaluation of Three-Dimensional Reconstruction-Based Compensation Methods in Myocardial Perfusion Spect", IEEE Transactions on Medical Imaging, vol. 21, No. 9, pp. 1040-1050, Sep. 2002.
David L. North et al., "Effective Half-Life of 131I in Thyroid Cancer Patients", Health Physics, vol. 81, No. 3, pp. 325-329, Sep. 2001.
Jen-Der Lin et al., "Papillary Thyroid Carcinomas with Lung Metastases", Thyroid, vol. 14, No. 12, pp. 1091-1096 (2004).
Johnathan R. Clark et al., "Variable Predicting Distant Metastases in Thyroid Cancer", The Laryngoscope, vol. 115, pp. 661-667, Apr. 2005.
C.M.L. West et al., "The Potential of Pet to Increase Understanding of the Biological Basis of Tumour and Normal Tissue Respnose to Radiotherapy", The British Institute of Radiology, PET Scanning in Radiotherpay, Supplement 28, pp. 50-54 (2005).
Hazel Breitz et al., "Dosimetry of High Dose Skeletal Targeted Radiotherapy (STR) with 166Ho-DOTMP", Cancer Biotherapy & Radiopharmaceuticals, vol. 18, No. 2, pp. 225-230 (2003).
Markus Cybulla et al., "End-Stage Renal Disease After Treatment with 90Y-DOTATOC", European Journal of Nuclear Medicine, vol. 28, No. 10, pp. 1552-1554, Oct. 2001.
David M. Goldenberg et al., "Antibody Pretargeting Advances Cancer Radioimmunodetection and Radioimmunotherapy", Journal of Clinical Oncology, vol. 24, No. 5, pp. 823-834, Feb. 10, 2006.
M. De Jong et al., "Therapy of Neuroendocrine Tumors with Radiolabeled Somatostatin-Analogues", The Quarterly Journal of Nuclear Medicine, vol. 43, No. 4, pp. 356-366, Dec. 1999.
Marion De Jong et al., "Somatostatin Receptor—Targeted Radionuclide Therapy of Tumors: Preclinical and Clinical Findings", Seminars in Nuclear Medicine, vol. 32, No. 2, pp. 133-140, Apr. 2002.
Magnus Tagesson et al., "A Monte-Carlo Program Converting Activity Distributions to Absorbed Dose Distributions in a Radionuclide Treatment Planning System", Acta Oncologica, vol. 35, No. 3, pp. 367-372 (1996).
H. Zaidi et al., "Therapeutic Applications of Monte Carlo Calculations in Nuclear Medicine", Philadelphi: Institus of Physics (2002) (345 pages).
J.E. Rail et al., "Radiation Pneumonitis and Firbrosis: A Complication of Radioiodine Treatment of Pulmonary Metastases from Cancer of the Thyroid", The Journal of Clinical Endocrinology and Metabolism, vol. 17, No. 11, pp. 1263-1276, Nov. 1957.
Alev K. Erdi et al., "Use of the Fast Hartley Transform for Three-Dimensional Dose Calculation in Radionuclide Therapy", Med. Phys., vol. 25, No. 11, pp. 2226-2233, Nov. 1998.
Timothy K. Johnson et al., "MABDOSE. I: Characterization of a General Purpose Dose Estimation Code", Med. Phys, vol. 26, No. 7, pp. 1389-1395, Jul. 1999.
A.A. Flynn et al., "Antibody and Radionuclide Characteristics and the Enhancement of the Effectiveness of Radioimmunotherapy by Selective Dose Delivery to Radiosensitive Areas of Tumour", International Journal of Radiation Biology, vol. 78, No. 5, pp. 407-415 (2002).
Abstract of K.S. Kolbert et al., "Dose-Volume Historgram Representation of Patient Dose Distribution in Three-Dimensional Internal Dosimetry", The Journal of Nuclear Medicine, vol. 35, No. 5, pp. 123P-124P, May 1994.
Richard S. Benua et al., "A Method and rationale for Treating Metastatic Thyroid Carcinoma with the Largest Safe Dose of 131I", Frontiers in Thryoidology, vol. 2, Plenum Medical Book Company, pp. 1317-1321, Sep. 1-6, 1985.
U.S. Appl. No. 14/438,132.
U.S. Appl. No. 15/132,590.
U.S. Appl. No. 14/170,020.
U.S. Appl. No. 12/514,853.
U.S. Appl. No. 12/514,853, filed Mar. 11, 2010, U.S. Pat. No. 9,387,344.
U.S. Appl. No. 12/687,670, filed Jun. 9, 2011, U.S. Pat. No. 8,693,629.
U.S. Appl. No. 12/690,471, filed Jul. 21, 2011, U.S. Pat. No. 8,914,237.
U.S. Appl. No. 12/820,852, filed Jun. 23, 2011, U.S. Pat. No. 8,688,618.
U.S. Appl. No. 13/335,565, filed Jun. 27, 2013, Pending.
U.S. Appl. No. 14/170,020, filed May 29, 2014, Abandoned.
PCT/US2013/072147, filed Nov. 27, 2013, Pending.
U.S. Appl. No. 14/438,132, filed Oct. 8, 2015, Pending.
U.S. Appl. No. 15/132,590, filed Oct. 6, 2016.
Sgouros, G., et al., "Three-dimensional Radiobiological Dosimetry (3D-RD) with 124I PET for 131I Therapy of Thryoid Cancer", European Journal of Nuclear Medicine and Molecular Imaging, vol. 38, No. Suppl. 1, (Apr. 12, 2011), pp. S41-S47.
Supplementary European Search Report issued in EP 13 84 8483 dated on Apr. 21, 2017.

* cited by examiner

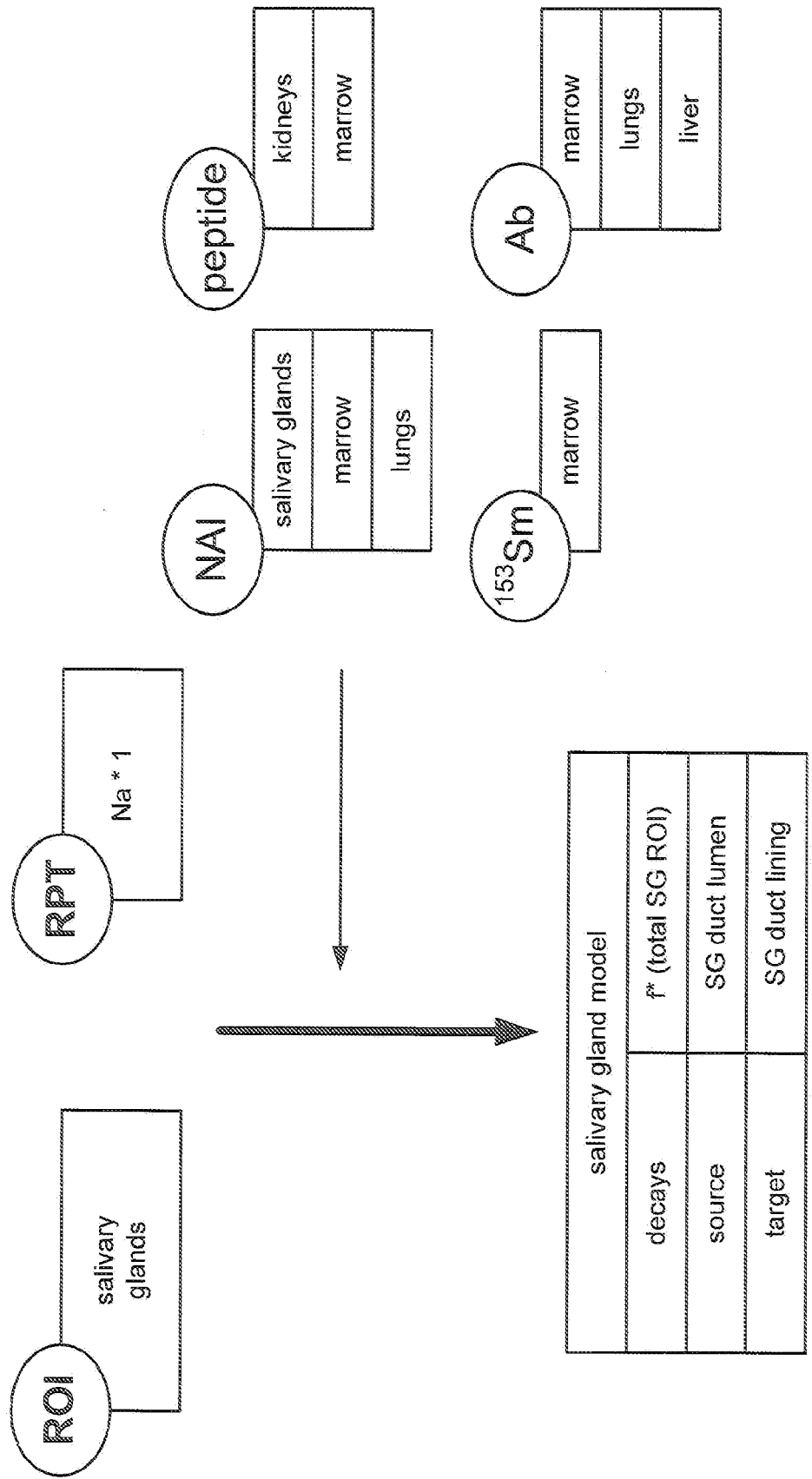

METHOD AND SYSTEM FOR ADMINISTERING RADIOPHARMACEUTICAL THERAPY (RPT)

CROSS REFERENCE TO RELATED APPLICATIONS

This application is related to U.S. patent application Ser. No. 12/687,670, filed Jan. 14, 2010; Ser. No. 12/690,471, filed Jan. 20, 2010; and Ser. No. 12/514,853, filed Sep. 15, 2009, the disclosures of which are incorporated by reference in their entireties.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 9 illustrates a micro to macro (m2m) database scheme, according to an embodiment.

DETAILED DESCRIPTION OF EMBODIMENTS

System and Method for Administering RPT

Figure 1:
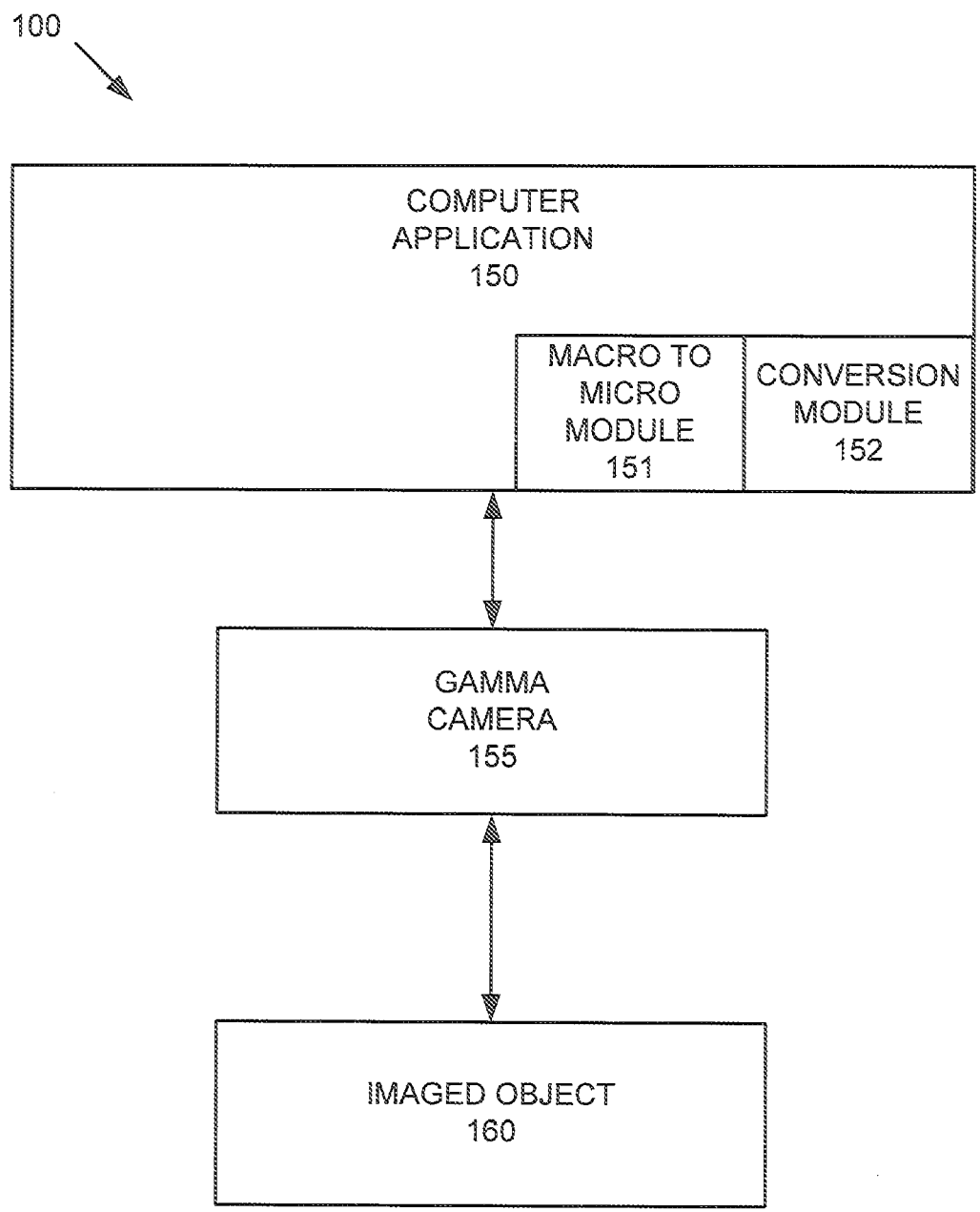
FIG. 1 illustrates a system 100 for administering radiopharmaceutical therapy (RPT), according to one embodiment.

Dosimetry can comprise the calculation of absorbed dose. Absorbed dose can be equal to energy imparted by radioactive substances divided by the mass of the target tissue and can be used to help determine the likely damage to tissue (e.g., organs, etc.). In, therapeutic nuclear medicine, in the "absorbed fraction" paradigm, the dose to a target region (e.g., an organ), used to ascertain likely toxicity to that region, may comprise dose contributions from all organs in the body which take up activity and whose emissions may deposit energy in the target organ. An equation that can describe this approach is the following:

$$D_t = \Sigma_s \frac{\tilde{A}_s \cdot \Delta \cdot \phi_{t \leftarrow s}}{m_t}.$$

In the above location, D can be the absorbed dose, $\tilde{A}_s$ can be the number of disintegrations in source volume s, $\Delta$ can be the energy per decay, $m_t$ can be the mass of target region t, and $\phi$ can be the absorbed fraction of energy originating in source volume s that is absorbed in target region t.

That is, the absorbed dose in a target region (e.g., an organ) can be equal to the sum of the dose contributions from all source organs in the body. Each contribution may be equal to the time integrated activity (e.g., number of decays), $\tilde{A}$, in the source multiplied by the energy per decay, $\Delta$, (isotope dependant) multiplied by the fraction of emitted energy, $\phi$, that originates in the source organ and is deposited in the target organ.

In order to facilitate the application of this formula, a library of results may be generated which incorporates the mass, absorbed fraction and energy per decay parameters into single values (S-values). This phantom model can allow the creation of a library of data from which dosimetric calculations can be made simply by knowing the number of decays in each body organ usually estimated by imaging. A software program which exploits this library and which can be used for estimating dose may be utilized (e.g., OLINDA/EXM, which is a commercially available software package that implements a dosimetry methodology that gives the average absorbed dose over a tissue or organ; it does not account, for patient-specific anatomy or radioactivity distribution within organs; it is also unable to provide patient-specific tumor absorbed dose estimates).

In one embodiment, when absorbed dose estimates on the macroscopic or whole-organ scale fail to predict response or toxicity, it may be necessary to perform dosimetry calculations on a smaller, functional or anatomical sub-unit scale. In such cases, the information needed may be on a scale that is substantially smaller than: the resolving power of clinical imaging detectors and modalities, or the scale of human organs; or both.

For example, α-particle emitters may be utilized for cancer therapy. Alphas may be highly effective (e.g., α-particle tracks can sterilize a cell, as opposed to the thousands of tracks necessary from β-articles), may not be susceptible to chemoresistance, or may be minimally susceptible to radioresistance, or any combination thereof. Despite the shorter range of α-particle emitters (as compared to traditional β-particle emitters) the linear energy transfer (LET), or energy deposited per unit length of as can be substantially (~1000×) larger than for β-particle emitters. Additionally, many potentially therapeutic α-particle emitters may decay to daughter α-particle emitters. The energy released by α-particle decay may be five to six orders of magnitude greater than the energy of the chemical bond used to attach an α-particle emitter to an antibody (e.g., via a metal chelator). Consequently daughter decay radionuclides may be released as free ions. If the decay occurs after the antibody has bound to the target cell and internalized, then the decay cascade may occur inside the target cell so that all four of the emitted alphas may bee within the target cell. If the daughters are short-lived this may make the decay highly potent and minimally susceptible to resistance mechanisms due to the combination of several emitted alphas so close to the nucleus (i.e., intracellularly) and also because of the high potency (i.e., capacity for. DNA double-strand breaks) of each α-particle emitter. The high potency may mean that an absorbed dose of 1 Gy from α-particles emitters may be three to seven times more cytotoxic (e.g., relative biological effect, or RBE) than the same absorbed dose from electrons or photons.

However, this multiplicity of α-particles can also cause additional toxicity if the daughter particles escape the cell confines and return to potential organs at risk via the blood stream before further disintegration. α-particle emitter therapy may be or become an active area of research and may become a part of the therapeutic armamentarium against cancer.

The amount of activity of a radiopharmaceutical administered to a patient for therapy may be optimized by effective dosimetry. Absorbed dose and the dose-rate-dependent radiobiological derived quantity biologic effective dose (BED) may correlate with normal organ toxicity; therefore the accurate calculation of these quantities may help provide optimal personalized therapy regimens for patients. Targeted α-emitter therapy may hold great promise as a cancer treatment but may also come with a great potential for toxicity. Understanding and correctly implementing the absorbed dose calculations to normal organs at risk may help guard from a sub-optimal implementation. Some cancer therapeutics that are effective against initial stage tumors (e.g., chemotherapy), may only be effective due to a closely monitored optimization of drug delivery. The threshold of effectiveness should be attained, while adhering to toxicity constraints. So it is with radiopharmaceutical therapy of solid and metastatic tumors. Achieving this delicate balance requires the most accurate dosimetry available.

FIG. 1 illustrates a system 100 for administering radiopharmaceutical therapy (RPT), according to one embodiment. Radiopharmaceutical therapy can comprise internal radionuclide therapy (IRT). In system 100, at least one detector (e.g., camera 155) images an imaged object 160 (e.g., a person, a phantom) and uses a computer application 110 to process information from the images. A camera 155 (e.g., positron emission tomography (PET) camera, gamma camera) can be a device used to image gamma radiation emitting radioisotopes. It can be used to view and analyze images of the human body or the distribution of radionuclides emitting gamma rays (e.g., to treat cancer). The camera 155 can be connected to a computer application 150 that can control the operation of the camera and/or the acquisition and storage of acquired images. The computer application 150 can accumulate events, or counts, of gamma photons that are absorbed by the crystal in the camera.

RPT can require accurate three dimensional dose calculations to avoid toxicity and evaluate efficacy. A treatment planning methodology can be performed using a patient-specific three-dimensional radiobiologic dosimetry package (3D-RD) for RPT using computer application 150. (More information on the 3D-RD and the algorithm can be found in U.S. patent application Ser. Nos. 12/514,853, 12/687,670, and 12/690,471, which are herein incorporated by reference.) Computer application 150 and its specific implementation within 3D-RD may provide the ability to utilize, individual patient images of the radioactivity distribution with images of anatomy and density (e.g., as obtained from computed tomography (CT) imaging) to calculate the spatial distribution of absorbed dose in a particular target region. Using radiobiological modeling, the absorbed dose distribution can be related to tumor control probability or probability of normal tissue compilations. Additionally, a parametric image of the spatial distribution of absorbed dose may be created that may adjust for differences between external radiotherapy (XRT) and radiopharmaceutical therapy (RPT) in the dose-rate at which total absorbed dose is delivered.

Computer application 150 may comprise: macro to micro module 151 and/or conversion module 152. The macro to micro modules 151 may translate macroscopically measured whole organ PK to microscopic sub-unit PK, as discussed in more detail below. The conversion module 152 may convert the animal model to the human model, as discussed in more detail below.

Figure 2:
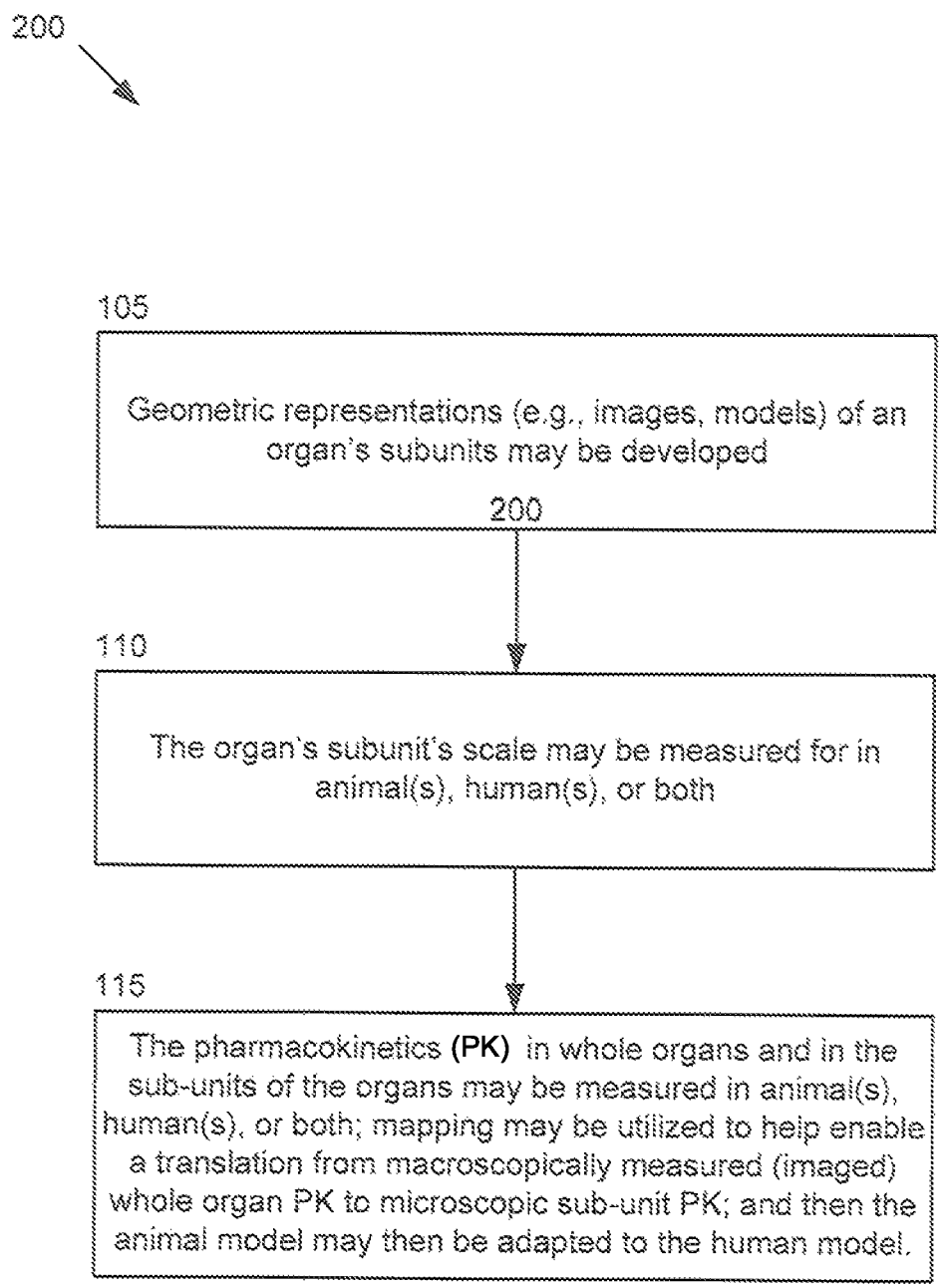
FIGS. 2 and 7 illustrate a method of calculating absorbed dose from, for example, a targeted alpha-emitter, according to one embodiment.
Figure 7:
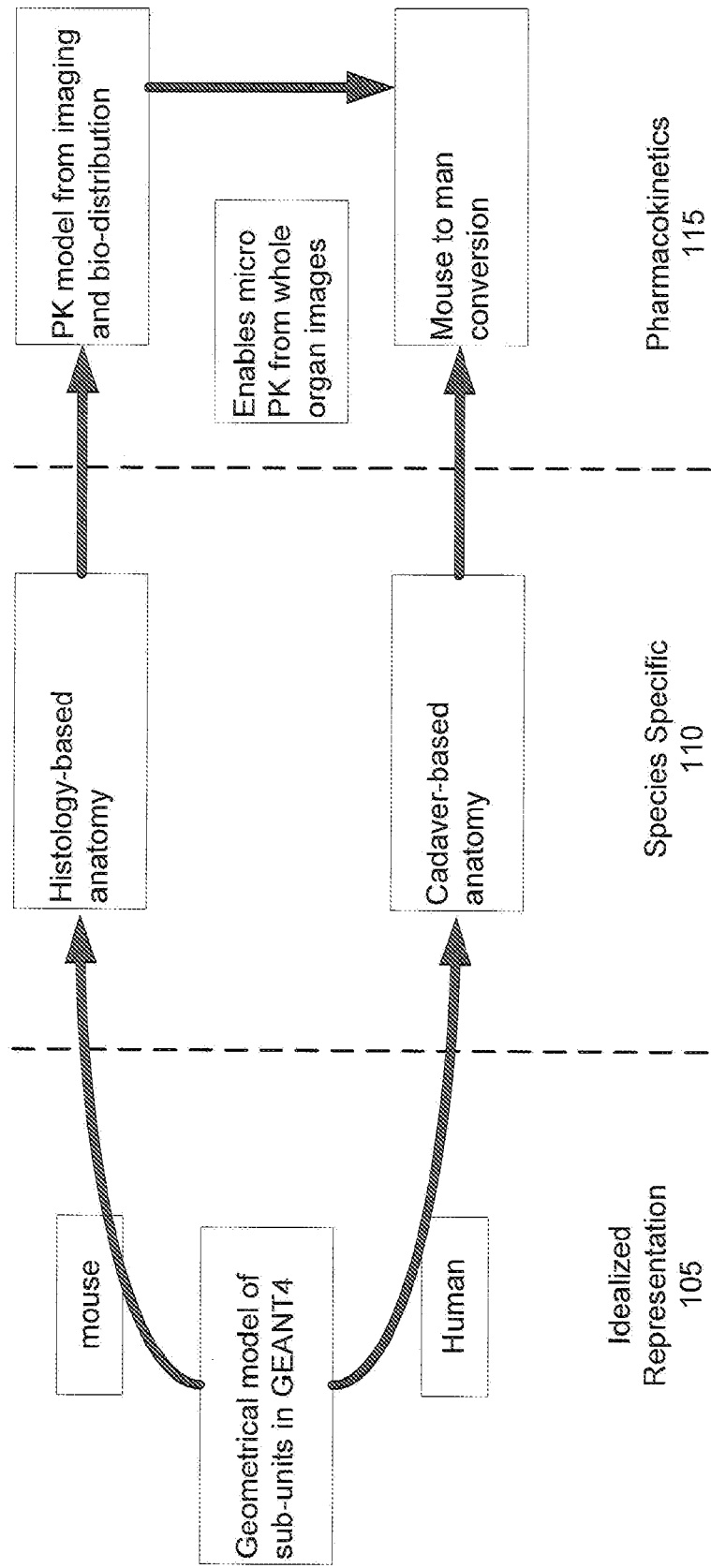

FIGS. 2 and 7 illustrate a method of calculating absorbed dose from, for example, a targeted alpha-emitter. In 105, geometric representations (e.g., images, models) of an organ's subunits may be developed. For example, geometric representations of marrow's and kidney's sub-units may be developed. The geometric representations may be scalable and implemented in, for example, the GEANT4 Monte Carlo code (i.e., the code needed to run MC on these structures will be generated). GEANT4 Monte. Carlo code is a generalized Monte Carlo package for simulating the passage of particles through matter. More information on GEANT4 can be found at the following web site, which is incorporated by reference: geant4.cern.ch/.

In 110, the organ's subunit's scale may be measured for in animal(s), human(s), or both. In one embodiment, the human scale may be measured in fresh cadavers to define the sub-unit anatomy for human organs as accurately as possible and provide a range of parameters. In some embodiments, time-integrated (e.g., time-independent) dose comparisons may be made. The time dependency of the dose may be incorporated by the addition of the requisite timing and compartmental modules in GEANT4.

In 115, the pharmacokinetics (PK) in whole organs and in the sub-units of the organs may be measured in animal(s), human(s), or both; mapping may be utilized to help enable a translation from macroscopically measured (imaged) whole organ PK to microscopic sub-unit PK; or the animal model may be adapted to the human model; or any combination thereof.

For example, the PK of the α-emitter labeled intact antibody and the α-emitting daughters in whole organs and in the sub-units of the organs may be measured in mice to help enable the conversion of macroscopically derived PK into microscopic kinetics applicable to the level of the sub-units. Since it may not be possible to extract tissue and perform autoradiography in humans to measure the PK at the sub-unit level, the modeled relationship between whole-organ (macro) and sub-unit (micro) PK measured in animals (e.g., mice) may be applied to humans.

Figure 8:
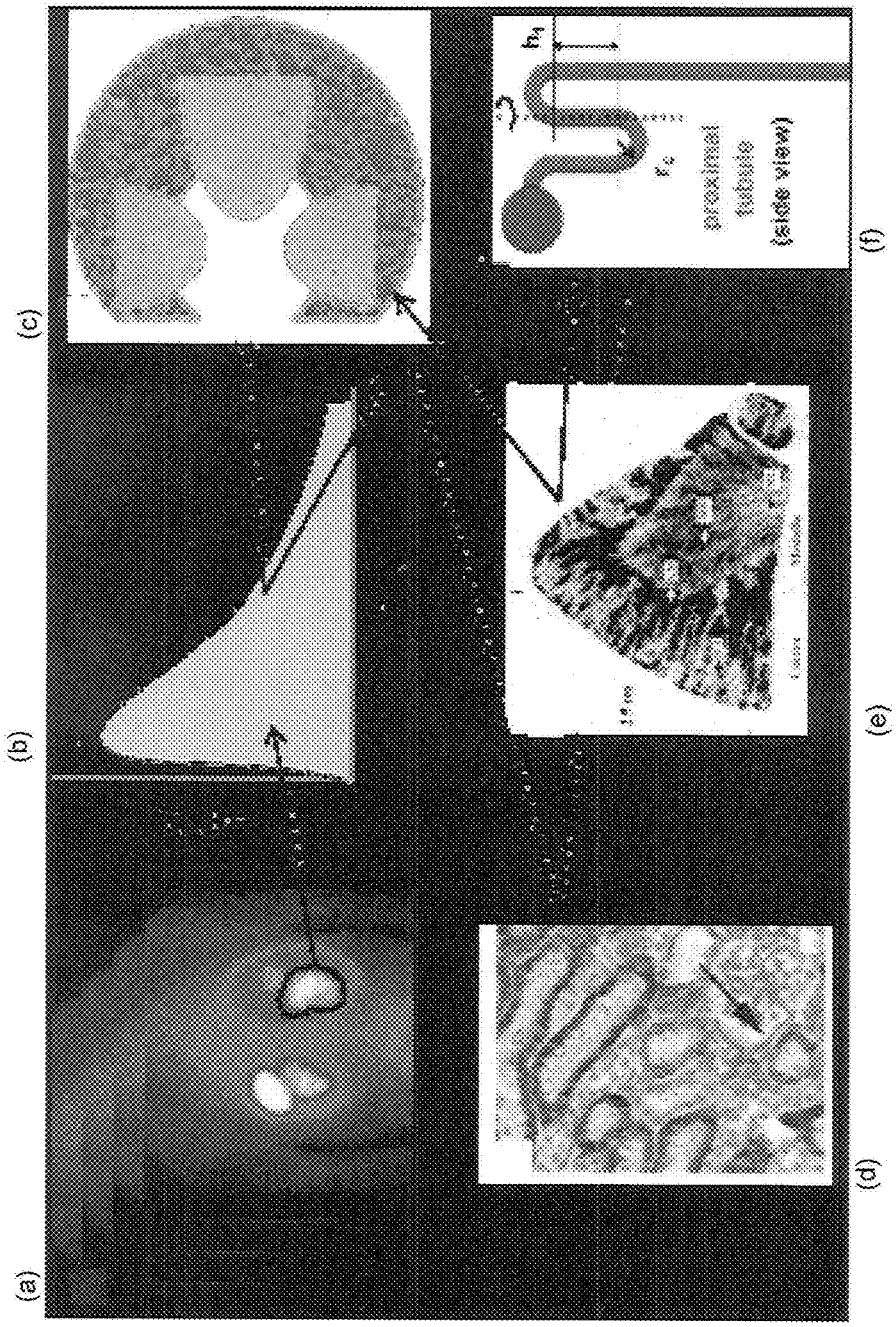
FIG. 8 illustrates an example of macro to micro calculations, according to an embodiment.

As mentioned above, mapping may be utilized to help enable a translation from macroscopically measured (imaged) whole organ PK to microscopic sub-unit PK. FIG. 8 illustrates an example of macro to micro calculations. Kinetics obtained from imaging (a) may be used to obtain the area under the whole organ curve (b). This may give the total number of decays occurring in the whole organ volume. Using information from the literature (e.g., molecular imaging methods comprising immunohistochemistry florescent microscopy, magnetic resonance imaging, microCT, or audioradiography or any combination thereof to show anatomy (d) and activity localization (e)), the micro-distribution and behavior of the agent in the tissue may be projected (c, f) and used in a micro scale model to calculate AD at the micro level by MC. As can be seen from the histology and autoradiography, the uniform appearance of activity in the kidneys (a) is, in fact, very non-uniformly distributed as the micro scale. The absorbed dose to the radiosensitive cells may be, therefore, not reflected form an average AD in this tissue/radiopharmaceutical combination.

Mathematically, the translation from macroscopically measured (imaged) whole organ PK to microscopic sub-unit PK may be translated as:

$$\tilde{A}_{organ} = \int_0^\infty A_{organ}(t)dt = \Sigma_{i,j} \int_0^\infty A_{ij}(t)dt.$$

Figure 6:
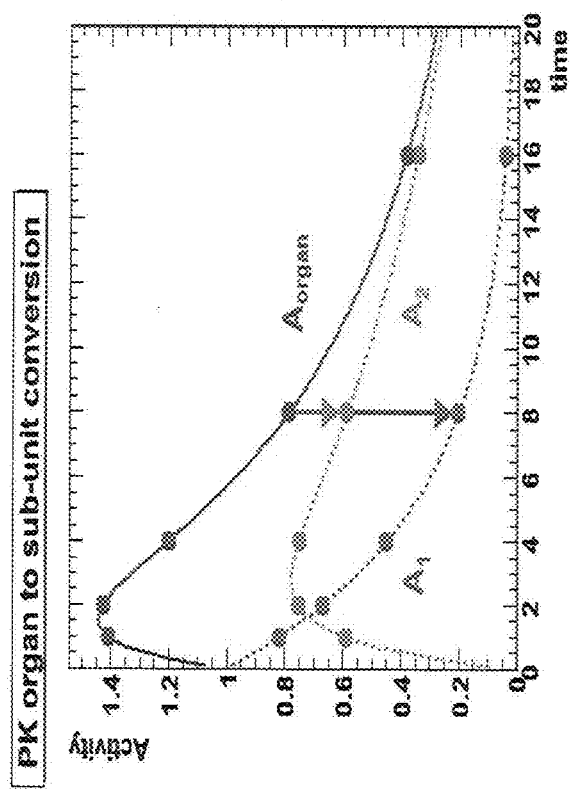
FIG. 6 illustrates the translation from macroscopically measured whole organ PK to microscopic sub-unit PK, according to one embodiment.

In the above formula, $\tilde{A}_{organ}$ can be the number of disintegrations in an organ, $A_{organ}$ can be the disintegration rate at a particular point in time t. The index i can iterate over the compartments making up the organ and the index j over the isotopes. By plotting the $A_{organ}$ and $A_{ij}$ values measured at different time points t, a graphical map such as the one shown in FIG. 6 may be established. This may help enabling a time-ordered PK conversion of macroscopically measured activity at multiple time points to the corresponding activity values at multiple time points in sub-compartments of the organ. In FIG. 7, a dual-compartment single isotope scenario is illustrated with functional fitting. The conversion shown by the arrows may also be at multiple time points and does not have to correspond to the time points used to create the conversion map. The individual $A_{ij(t)}$ values may then be allocated to the sub-unit models based upon the ratio of individual sub-unit volume to volume of occupancy within the whole organ.

FIG. 8 illustrates a micro to macro (m2n) database scheme, according to an embodiment. A dosimetry software package such as 3D-RD may query a web-accessible database that is keyed according to tissue and radiopharmaceutical (or radiopharmaceutical class). If a match is found, the database may identify the appropriate module for performing the micro-scale or cell-scale calculation. In this way, patient-specific macrocopic measurements may be used to perform micro-scale dosimetry calcuations. These m2m modules may be developed using information obtained from studies that describe the micro-level distribution of different normal organ/therapeutic radiopharmaceutical combination and also from a general understanding of the properties of different classes of radiopharmaceuticals.

FIG. 9 illustrates a flow chart for the process of performing micro scale calculations for the example of a $Na^{131}I$ salivary gland. A match in ROI and RPT entries with one of the module libraries (NAI, peptide, $^{153}Sm$ and antibody (ab) arc shown as examples) may bring up the proposed micro-level calculation described in the salivary gland (SG) model table. A fraction of the decays obtained from the ROI may be assigned to SG duct lumen and the dose to the SG duct wall may be calculated. Reference geometrical models of the relevant anatomy, corresponding volumes, and apportionment factors, f, may be developed and used in a Monte Carlo or point-kernel calculation within 3D-RD.

As also mentioned above, the animal model may be adapted to the human model. For example, the mouse model may be extrapolated to a human models. For a representative sample size of time points (e.g., 2x-3x more than used to create the conversion map), the equation below may be used to convert mouse model derived organ and sub-compartment PK to corresponding human organ sub-compartment PK:

$$\frac{A_{organ}(M, t, p)}{A_{ij}(M, t, p)} = \frac{A_{organ}(m, t)}{A_{ij}(m, t)} \cdot \frac{f_{occ}(M, p)}{f_{occ}(m)}$$

where the ratio on the left side of the equation may represent the ratio of compartmental activities ($A_{ij}$) to the measured activity ($A_{organ}$) at time t in the human (M). Note that p may represent other parameters not explicitly shown in the equation (e.g., parameters that may be needed to account for differences in nephron occupancy factor in different patients, depending upon the patient's age, the patient's sex, the patient's prior treatment history, or any combination thereof). This may be equal to the same ratios in the mouse (m) adjusted for measured fraction of occupancies in the two species. This does not necessarily imply an identical functional form of the total measured activity in the human versus the mouse.

FIGS. 2 and 7 thus illustrates a methodology that integrates sub-organ modeling, according to an embodiment of the invention. This methodology may be suited for α-particle therapy in some embodiments. The absorbed fraction paradigm may give average dose to an organ, may not account for local deposition of dose, and may be insensitive to the temporal aspects of pharmacokinetics and cell mobility. This absorbed fraction paradigm may rely on the relatively long-ranged energy deposition typical of β- and γ-particle emitters. However, the range of α-particles may be only a few cell diameters long. Local uptake of activity driven by biological imperatives that exist at the functional sub-unit level may be taken into account for effective and safe α-particle emitter therapy.

This dosimetry methodology 200 of FIG. 2 may be utilized with α-particles. In some embodiments, this dosimetry methodology 200 may be founded on Monte Carlo modeling within the GEANT4 framework, accurate 3-dimensional anatomical data from human cadavers, or pharmacokinetics established in animal models (e.g., mouse models), or any combination thereof. In addition, in normal organs, the spatiotemporal distribution needed to utilize absorbed fractions defined at the microscopic level may be obtained from macroscopic measurements by apportioning the macroscopic distribution to different microscopic compartments for a given radiopharmaceutical agent. In addition, the link between macroscopic and microscopic spatiotemporal relationship for a given agent measured in a pre-clinical model may be applied to a human because the distribution of the agent to the different microscopic compartments should remain the same. Specific adjustments for scale and known pharmacological/physiological differences may improve the translation to the human.

The dosimetry methodology 200 may provide specific models for organs most at risk of toxicity in the existing pre-clinical and clinical α-particles experiments. In the examples set forth below (e.g., marrow, kidney) dose distribution may be determined in the functional and anatomical sub-units, but results may be provided at the cellular level within each sub-organ compartment.

EXAMPLES

Marrow Example. Bone marrow may be the dose-limiting organ in radioimmunotherapy. Accurate dosimetry of bone marrow may be difficult because of its complex geometry and the presence of tissue inhomogeneities. For example, bone marrow may be modeled, and the model may comprise a Monte Carlo simulation of an α-particle emitter decay in an idealized marrow cavity unit (a simple sphere) of, for example, radius 250-500 μm, with an endosteal layer 10 μm thick. (See, e.g., FIG. 3B). This model may be of particular relevance for 223Ra, which may localize to the endosteal layer. The energy from the simulation may be collected and the dose to each bone marrow cell may be calculated.

Chord length distributions from human cadavers may be used to generate realistic geometries. The human anatomical information may be gathered from cadavers for anatomical accuracy and may be used to provide an array of parameters that reflect human diversity. For example, a comprehensive library of microCT images of trabecular spongiosa for internal dosimetry calculations may be used, comprising libraries for: an 18-year old male, 40-year male, 45-year female, 64-year male, and 66-year female. Modeled regions may include the bone trabeculae, the 10-μm layer of endosteum, and 50-μm layer of shallow marrow, a remaining layer of deep marrow. Labeled cellular voxelized units may include the marrow adipocytes, osteoblasts, osteoclasts, osteoprogenitor cells, hematopoietic stem and progenitor cells, supporting marrow structures, and blood sinuses and vessels. The spatial distribution of HSPC may be based upon CD34+ histology studies (e.g., by Bourke et al. (50)). Confirmatory MCNPX simulations of alpha-particle transport for comparison to the GEANT4 results may also be utilized.

Kidney Example. Renal toxicity may be a concern for toxicity for low molecular weight constructs, such as those used in radiopeptide therapy of neuroendocrine tumors. Since peptides, other low molecular weight antibody constructs, and heavy metalloid atoms (α-emitters) may be mainly deposited in the renal cortex, which is associated with a greater radiobiological sensitivity, the localization of the absorbed dose may increase the risk of renal toxicity. However, the range of α-particle emissions means that even the delineation between renal cortex, medulla, and pelvis is insufficient to explain the elevated levels of renal toxicity observed in experimental murine studies. Indeed, considering that the functional sub-unit of the kidney is the nephron, an entity whose dimensions are comparable to those of the range of emitted α-particles, a model of toxicity based on the nephron, including uptake at the cellular level, rather than the whole kidney, may be useful.

Figure 3A:
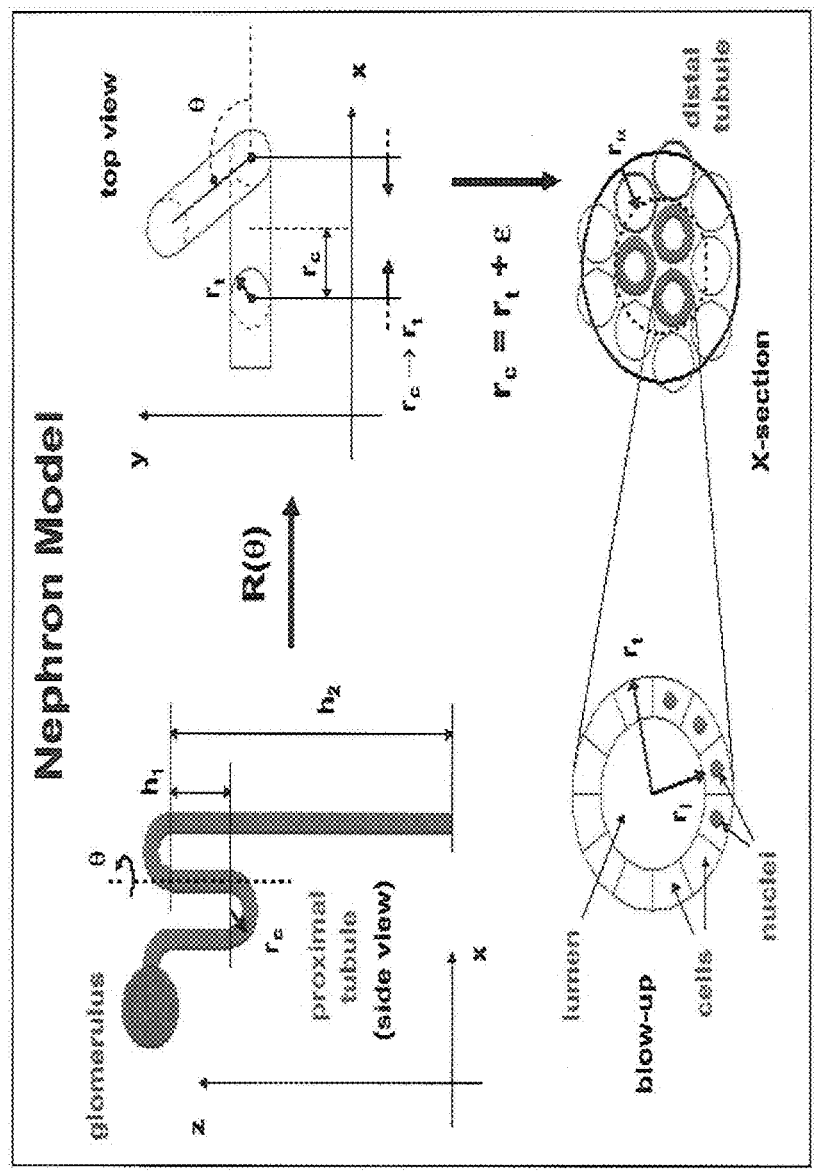
FIG. 3A illustrates a nephron model, according to one embodiment.
Figure 3B:
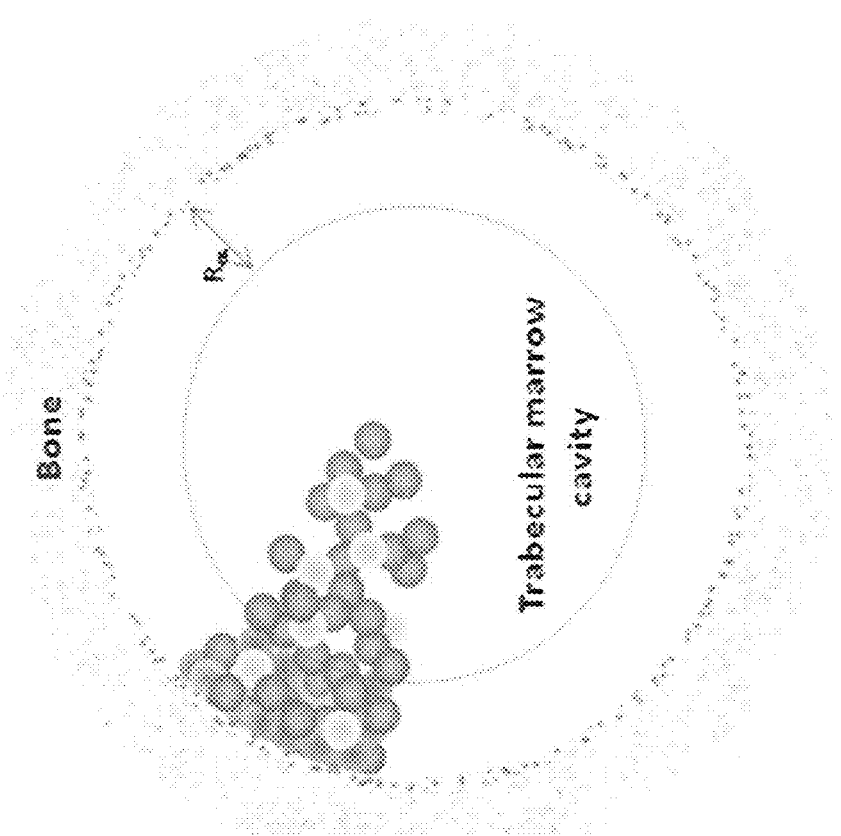
FIG. 3B illustrates a model of a bone comprising a Monte Carlo simulation, according to one embodiment.

A simple idealized nephron model may use simple geometrical shapes (cylinders, spheres and toroids) and may be initially based on parameters taken from medical textbooks. FIG. 3A illustrates a nephron model. The proximal tubule may be the region where the free metalloids are most likely to be absorbed; and together with the glomerulus, they may be the regions which exhibit toxicity in murine studies of renal toxicity due to $^{225}$Ac therapy. The glomerulus may be modeled as a simple sphere, the proximal tubule as hollow cylinders and toroids through which the fluid to be filtered is passed. Proximal tubules may be typically convoluted as they first leave the glomerulus before the tubule descends as the descending loop of Henle. The tubule (and glomerulus) in FIG. 3A has also been subdivided into individual cells. For the tubule, these comprise simple cuboidal epithelial cells. Because the range of the α-particles is slightly larger than the tubule radius, nearest neighbor tubules may also be taken into account in the dosimetry. Some tubules will be distal may be modeled containing no activity.

Figure 4:
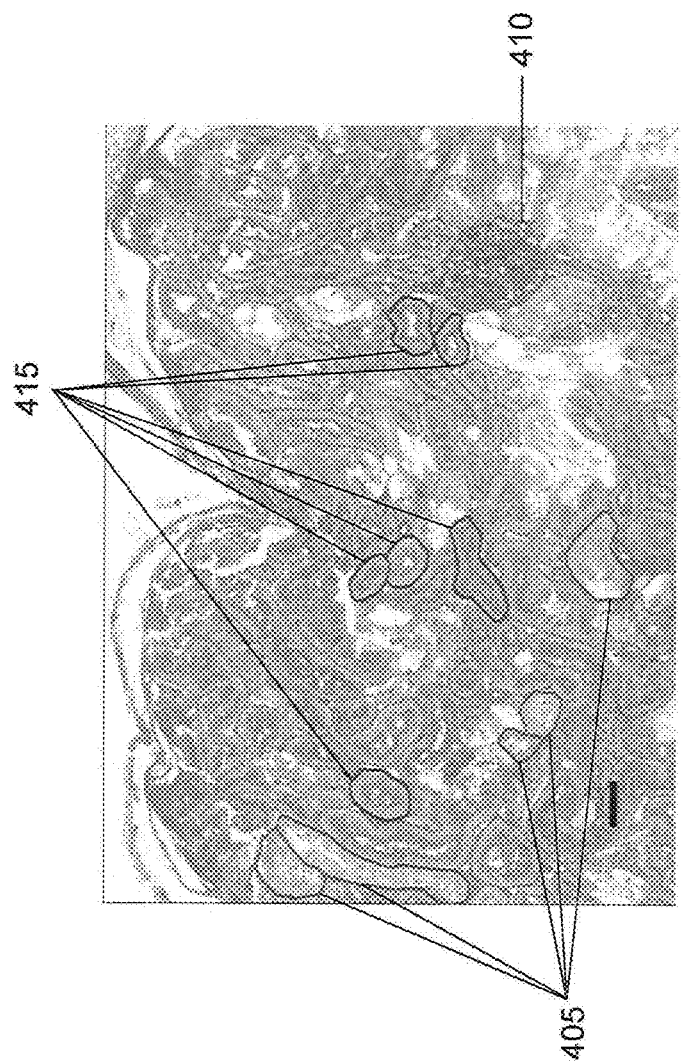
FIG. 4 illustrates a cross-section of a mouse kidney that was stained with periodic acid Schiff (PAS) stain, according to one embodiment.

FIG. 4 illustrates a cross-section of a mouse kidney that was stained with periodic acid Schiff (PAS) stain. PAS positive material shows up along the brush border (lumen surface) of the proximal tubules (see examples of 415). Note that basement membrane material outside the tubular epithelium is also PAS positive, but not specific for proximal tubules (see examples of 405). Also note the glomeruli are distinguishable (see example of 410).

Figure 5:
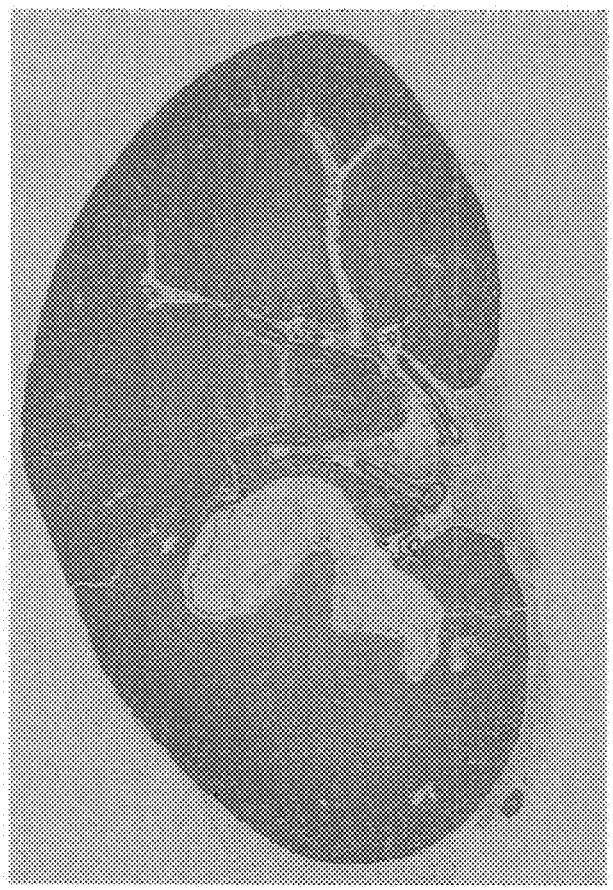
FIG. 5 illustrates a composite (e.g., stitched) slide of murine kidney slice, according to one embodiment.

The ratio of dose from the nephron model to dose from the kidney model depends in a critical way upon the percentage of volume, or fraction of occupancy ($f_{occ}$) allocated in the kidney to the sub-units (e.g., proximal tubules and glomeruli). For example, from contours drawn on five different images from five kidney cross-section slides each (25 total), preliminary $f_{occ}$s for the proximal tubule, distal tubules (both with (81%) and without (66%) lumen space) and glomeruli (2.3%) within the whole kidney and cortex may be established, and may contribute to a greater accuracy as well as providing theoretical constraints for quality control. These values will be improved upon with a more representative selection of slices (~50 per kidney). For example, the use of a microscope (e.g., Nikon 600 HL microscope) and software (e.g., NIS-Elements BR software, which is a commercially available software package for image analysis; more information may be found at the following web site, which is herein incorporated by reference: http://www.nis-elements.com/) may help stitch together magnified images into a single slice image. For example, FIG. 5 illustrates a composite (e.g., stitched) slide of murine kidney slice from 20 separate images.

The establishment of the full human kidney model may involve using human cadaver data to establish full 3-dimensional anatomically accurate and diverse (e.g., for different kidneys sizes) models for comparison with the idealized geometrical models. Here too, given that kidney mass has been shown to be a vital factor in establishing dose-response (e.g., BED-toxicity response) for kidneys in radio peptide planned therapy of neuroendocrine tumors, a kidney mass depended array of geometric models may be used whose results may be interpolated either functionally or with linear segments for a dosimetric model whose inputs may be kidney mass as well as whole organ pharmacokinetics from several time point imaging.

To obtain high-resolution images of the human kidney for α-particle transport modeling, in one embodiment, human kidneys may be acquired and imaged at high resolution under nuclear magentic resonance (NMR) microscopy. For example, imaging studies may be conducted at the widebore. 17.6 T (750 MHz) NMR spectrometer within the Advanced Magnetic Resonance Imaging and Spectrometry (AMRIS) facility in. the University of Florida's McKnight Brain Institute. A voxel image resolution of between 10 to 50 μm may be targeted for model construction. Multiple human kidney samples may be sought. Kidneys sought for imaging may include kidneys where one can study more macroscopic variations in kidney structure such as the overall and relative sizes of the cortex/medullary and number of medullary pyramids. These images may be compared to in-vivo MR images of the kidneys of the Visible Human Project (http://en.wikipedia.org/wikiNisible_Human_Project) to confirm no gross anatomical changes following tissue embalming. A supplemental set of cross-sectional histology images may be prepared following MR microscopy.

Images for which normal anatomy is captured may be segmented in a voxelized format for GEANT4 simulations. Two versions of the model may be implemented. One model may comprise the entire organ showing regions of the renal cortex, each individual medullary pyramid, and the renal pelvis. A higher-resolution regional kidney model may also be constructed from a Volume of Interest (VOI) of perhaps several localized medullary pyramids and surrounding renal cortex in which individual nephrons and collecting ducts may be segmented. As needed, supplemental NURBS (nonuniform rational B-spline) surface models of the glomerular capsule and proximal/distal renal tubules may be created, based upon the imaged anatomy, and then inserted within the final voxelized kidney model. Final model format, spatial extent, and functional unit definition may also be devised.

CONCLUSION

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above-described exemplary embodiments.

In addition, it should be understood that the figures described above, which highlight the functionality and advantages of the present invention, are presented for example purposes only. The architecture of the present invention is sufficiently flexible and configurable, such that it may be utilized in ways other than that shown in the figures.

For consistency reasons, used the phrase "comprising" throughout the claims instead of "including, but not limited to". However, it should be noted that "comprising" should be interpreted as meaning "including, but not limited to".

In addition, it should be noted that, if not already set forth explicitly in the claims, the term "a" should be interpreted as "at least one" and "the", "said", etc. should be interpreted as "the at least one", "said at least one", etc.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The invention claimed is:

1. A computerized method for determining an optimum amount of radiopharmaceutical therapy (RPT) to administer, comprising:
   performing processing associated with obtaining, with a detector, macroscopic activity image information related to an agent for an imaged organ for a first species and a second species;
   performing processing associated with obtaining, with the detector, microscopic activity image information related to the agent for the imaged organ for the second species;
   performing processing associated with running calculations, using a computer application, using the macroscopic activity image information for the second species and the microscopic activity image information for the second species to derive microscopic activity image information for the first species;
   performing processing related to running calculations, using the computer application, using the microscopic activity image information for the first species to derive microscopic absorbed dose rate image information for the first species, wherein a uniform distribution at a microscopic level of the agent is not assumed in the first species;
   performing processing associated with running calculations, using the computer application, using the microscopic absorbed dose rate information for the second species to derive RPT macroscopic absorbed dose image information and microscopic absorbed dose image information for the imaged organ in the first species;
   performing processing associated with running calculations, using the at least one computer application, using the RPT macroscopic absorbed dose rate information and the microscopic absorbed dose image information to derive the optimum amount of RPT to administer to the first species; and
   performing processing associated with outputting, using the at least one computer application, the optimum amount of RPT to administer to the first species.

2. The method of claim 1, wherein:
   molecular imaging methods are utilized to provide distribution of a therapeutic agent;
   the RPT comprises internal radionuclide therapy (IRT);
   uncertainty evaluation is performed;
   the one detector is at least one camera; or
   the calculations comprise a Monte Carlo simulation; a point kernel convolution; or both; or
   any combination thereof.

3. The method of claim 2, wherein the molecular imaging methods comprising immunohistochemistry, florescent microscopy, magnetic resonance imaging, microCT, or audioradiography, or any combination thereof.

4. The method of claim 1, wherein the imaged organ for the second species is from an animal and/or the animal is a mouse.

5. The method of claim 4, wherein the first species is human, and/or wherein the RPT total absorbed dose image information for the imaged organ of the at least one animal is used to determine RPT total absorbed dose image information for an organ for a human organ.

6. The method of claim 4, wherein microscopic absorbed dose rate information for multiple times is obtained and utilized.

7. The method of claim 1, wherein obtaining the macroscopic activity image information and/or the microscopic activity image information further comprises:
   performing processing associated with obtaining at least two anatomy images relating to anatomy of an imaged object;
   performing processing associated with obtaining multiple images regarding radioactivity distribution over time; and
   performing processing associated with combining each radioactivity image with each anatomy image to create activity image information.

8. The method of claim 7, further comprising: performing processing associated with registering the anatomy images related to the radioactivity distribution over time.

9. The method of claim 1, further comprising: performing processing associated with adjusting, using the at least one computer application, the optimum amount of RPT to administer.

10. The method of claim 9, wherein the performing processing associated with adjusting accounts for any already delivered doses.

* * * * *

UNITED STATES PATENT AND TRADEMARK OFFICE
CERTIFICATE OF CORRECTION

PATENT NO. : 9,757,084 B2
APPLICATION NO. : 13/335565
DATED : September 12, 2017
INVENTOR(S) : George Sgouros and Robert Hobbs It is certified that error appears in the above-identified patent and that said Letters Patent is hereby corrected as shown below:

In the Specification

Column 1, Line 4, insert the following:
--STATEMENT OF GOVERNMENTAL INTEREST
This invention was made with government support under grant number CA116477, awarded by the National Institutes of Health and grant number DE-FG02-05ER63967, awarded by the Department of Energy. The government has certain rights in the invention.--

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*